United States Patent
Kim

(10) Patent No.: US 10,169,532 B2
(45) Date of Patent: Jan. 1, 2019

(54) QUERY SEQUENCE GENOTYPE OR SUBTYPE CLASSIFICATION METHOD

(75) Inventor: Sang-Soo Kim, Seoul (KR)

(73) Assignee: OMICSIS, INC., Daejeon (KR)

( * ) Notice: Subject to any disclaimer, the term of this patent is extended or adjusted under 35 U.S.C. 154(b) by 873 days.

(21) Appl. No.: 13/581,338

(22) PCT Filed: Aug. 13, 2010

(86) PCT No.: PCT/KR2010/005337
§ 371 (c)(1),
(2), (4) Date: Mar. 14, 2013

(87) PCT Pub. No.: WO2011/105667
PCT Pub. Date: Sep. 1, 2011

(65) Prior Publication Data
US 2013/0226466 A1    Aug. 29, 2013

(30) Foreign Application Priority Data
Feb. 26, 2010 (KR) ................ 10-2010-0017999

(51) Int. Cl.
G06F 19/20   (2011.01)
G06F 19/24   (2011.01)
G06K 9/62    (2006.01)
G06F 19/22   (2011.01)

(52) U.S. Cl.
CPC .......... *G06F 19/24* (2013.01); *G06K 9/6234* (2013.01); *G06K 9/6284* (2013.01); *G06F 19/22* (2013.01)

(58) Field of Classification Search
CPC .......... G06F 19/20; G06F 19/22; G06F 19/24; G06K 9/6234; G06K 9/6284
See application file for complete search history.

(56) References Cited

PUBLICATIONS

International Search Report issued in PCT/KR2010/005337 dated May 19, 2011.
Myers, et al., "A statistical model for HIV-1 sequence classification using the subtype analyser (STAR)", Bioinformatics, vol. 21, No. 17, pp. 3535-3540, 2005.
Gifford, et al., "Assessment of automated genotyping protocols as tools for surveillance of HIV-1 genetic diversity", AIDS, vol. 20, No. 11, pp. 1521-1529, Jul. 2006.
Wu, et al., "Nucleotide composition string selection in HIV-1 subtyping using whole genomes", Bioinformatics, vol. 23, No. 14, pp. 1744-1752, May 2007.

(Continued)

*Primary Examiner* — Mary K Zeman
(74) *Attorney, Agent, or Firm* — Studebaker & Brackett PC

(57) ABSTRACT

The present invention relates to a method for classifying genotype or subtype of query sequence. More particularly, the present invention is directed to a method for classifying genotype or subtype of query sequence, comprising: (i) selecting base sequences of various viruses of which genotypes or subtypes are known as reference sequences and obtaining a distance matrix by calculating distances between sequences in a multiple alignment of said reference sequences; and (ii) developing a discriminant equation which may classify the reference sequences by performing discriminant analysis for a cluster obtained by clustering said reference sequences through multidimensional scaling of the distance matrix, followed by classifying genotype or subtype of a query sequence according to said discriminant equation.

4 Claims, 30 Drawing Sheets

Specification includes a Sequence Listing.

(56) References Cited

PUBLICATIONS

Zhang, et al., "jpHMM at GOBICS: a web server to detect genomic recombinations in HIV-1", Nucleic Acids Research, vol. 34, W463-W465, Jul. 2006.

De Oliveira, et al., "An automated genotyping system for analysis of HIV-1 and other microbial sequences", Bioinformatics, vol. 21, No. 19, pp. 3797-3800, Aug. 2005.

Janini, et al., "Human Immunodeficiency Virus Type 1 DNA Sequences Genetically Damaged by Hypermutation are Often Abundant in Patient Peripheral Blood Mononuclear Cells and may be Generated During Near-Simultaneous Infection and Activation of CD4 + T Cells", J. Virol. 2001, 75(17): 7973-7986.

Gandhi, et al., "Role of APOBEC3G/F-Mediated Hypermutation in the Control of Human Immunodeficiency Virus Type 1 in Elite Suppressors", J. Virol. 2008, 82(6): 3125-3130.

Land, et al., "Human Immunodeficiency Virus (HIV) Type 1 Proviral Hypermutation Correlates with CD4 Count in HIV-Infected Women from Kenya", J. Virol., 2008, 82(16): 8172-8182.

Fig. 7a

Genotype/Subtype Prediction Service

Paste a sequence in FASTA FORMAT       Virus, Sequence Type: [HIV-1 nucleotide ▼]

```
>gi|109966992|gb|DQ518465.1| HIV-1 isolate 74052 from Brazil pol protein (pol)
gene, partial cds
CCTCAATCACTCTTTGGCAACGACCCACTCGTCACAATAAAGTAGGGGGGCAACTAAAGGAAGCTCTAT
TAGATACAGGAGCAGATGATACAGTATTAGAAGAAATGAGTTTGCCAGGAAGATGGAAACCAAGAATGAT
AGGGGAATTGGAGGTTTTATCAAAGTAAGACAGTATGATCAGATAGTCAGATAATTTGCGGACATAAA
GCTGTAGGTACAGTATTAGTAGGACCTACACCTGTCAACATAATTGGAAGAAATTTGTTGACTCAGATTG
GCTGCACTTAATTTTCCCATCAGTCCTATTGAAACTGTACCAGTAAAATTAAGCCAGGAATGGATGG
CCCAAAAGTTAAACAGTGGCCATTGACAGAAGAAAAAATAAAAGCATTAGTAGAAATTTGTACAGAATG
GAAAAAGGAAGGAAAAATTTCAAAATTGGGCCTGAAAACCCATACAATACTCCAGTATTTGCCATAAGA
AAAAGACAGTACTAAATGGAGAAAATTAGTAGATTTCAGAGAACTTAATAAAAGAACTCAAGACTTCTG
``` or select a FASTA FILE: [                    ]

or select an EXAMPLE: [NCBI GI: 18310281 HIV-1 isolate 74052 from Brazil (pol) ▼]   [SEARCH]

Gene: [Unknown ▼]       Handling GAPS: [Delete all sites that include gaps ▼]

Multiple substitution correction algorithm: [Jukes-Cantor ▼]

MDS Dimensionality - Major: [10 ▼] - Nested: [10 ▼]       [RESET] [SUBMIT]

Copyrighted by Bio-Data Mining Lab, Department of Bioinformatics and Life Sciences, Soongsil University, Seoul, Korea

Fig. 7b

Virus : HIV-1 / Sequence Type : Nucleotide

Sequence Description: gi|100966992|gb|DQ5

Multiple Substitution Correction Algorithm : Jukes-Cantor

All sites that include gaps were deleted.

Gene by Gene Subtype Prediction Summary

| Gene | Start | Stop | Length | Major Subtype | Nested Analysis | Final Decision |
|------|-------|------|--------|---------------|-----------------|----------------|
| pol  | 0     | 1497 | 1356   | B             | B               | B (Unambiguous Nested) |

Detailed result for pol (major) | Outlierness: 0.6641302341933346 (all), 1.21333861312732 (group)

Fig. 7c

Cross-validation of Discriminant Models

Miss-Classification Rate: 2 / 735 at 10 Dimensional MDS

Predicted

| Objective | 01_AE | A | B | C | D | F | G | H | J | K |
|---|---|---|---|---|---|---|---|---|---|---|
| 01_AE | 57 | 0 | 0 | 0 | 0 | 0 | 0 | 0 | 0 | 0 |
| A | 0 | 58 | 0 | 1 | 0 | 0 | 0 | 0 | 0 | 0 |
| B | 0 | 0 | 168 | 0 | 0 | 0 | 0 | 0 | 0 | 0 |
| C | 0 | 0 | 0 | 371 | 0 | 0 | 0 | 0 | 0 | 0 |
| D | 0 | 0 | 0 | 0 | 46 | 0 | 0 | 0 | 0 | 0 |
| F | 0 | 0 | 0 | 0 | 0 | 12 | 0 | 0 | 0 | 0 |
| G | 0 | 0 | 0 | 0 | 0 | 0 | 16 | 0 | 0 | 0 |
| H | 0 | 0 | 0 | 0 | 0 | 0 | 0 | 3 | 0 | 0 |
| J | 0 | 0 | 0 | 0 | 0 | 0 | 0 | 0 | 0 | 0 |
| K | 0 | 0 | 0 | 0 | 0 | 0 | 0 | 0 | 0 | 2 |

| Download | Multiple Alignment | Distance Matrix | GGobi XML |
|---|---|---|---|

| Subtype | Posterior Probability |
|---|---|
| 01_AE | 9.71109885943648e-91 |
| A | 1.80656423694821e-74 |
| B | 1 |
| C | 7.31846765875173e-85 |
| D | 7.43938556882024e-43 |
| F | 5.52620940539233e-47 |
| G | 4.22865452716726e-88 |
| H | 1.32463676840249e-31 |
| J | 2.11795348348139e-43 |
| K | 9.23103997790027e-30 |

QUERY SEQUENCE GENOTYPE OR SUBTYPE CLASSIFICATION METHOD

This application is the U.S. National Phase of, and Applicants claim priority from, International Application Number PCT/KR2010/005337 filed Aug. 13, 2010 and Korean Patent Application No. KR 10-2010-0017999 filed Feb. 26, 2010, each of which are incorporated herein by reference.

TECHNICAL FIELD

The present invention relates to a method for classifying genotype or subtype of query sequence. More particularly, the present invention is directed to a method for classifying genotype or subtype of query sequence, comprising: (i) selecting base sequences of various viruses of which genotypes or subtypes are known as reference sequences and obtaining a distance matrix by calculating distances between sequences in a multiple alignment of said reference sequences; and (ii) developing a discriminant equation which may classify the reference sequences by performing discriminant analysis for a cluster obtained by clustering said reference sequences through multidimensional scaling of the distance matrix, followed by classifying genotype or subtype of a query sequence according to said discriminant equation.

BACKGROUND ART

Accurate genotyping (or subtyping) is critical in understanding evolution of divergent viruses. Recently, rapid growth in the number of viral sequences in the public databases is observed. For example, HIV-1 and HCV sequence entries NCBI GenBank have doubled almost every three years. These viruses also show great genotypic diversities and thus have been classified into groups, so-called genotypes and subtypes (Robertson et al., 2000; Simmonds et al., 2005).

Consequently, genotyping (or subtyping) these virus strains based on their sequence similarities has become one of the most basic steps in understanding their evolution, epidemiology and developing antiviral therapies or vaccines.

The conventional subtyping methods include the following: (1) the nearest neighbor methods that look for the best match of the query to the representatives of each subtype, so-called references; (2) the phylogenetic methods that look for the monophyletic group to which the query branches. Since the subtypes have been defined originally as separately clustered groups, these intuitively sound methods have been widely used and quite successful for many cases.

However, with increasing numbers of sequences, outliers that cannot be clearly subtyped or for which these methods do not agree are being observed. A recent report that compared these different automatic subtyping methods with HIV-1 sequences showed less than 50% agreement among them except for subtypes B and C (Gifford R, de Oliveira T, Rambaut A, Myers R E, Gale C V, Dunn D, Shafer R, Vandamme A M, Kellam P, Pillay D: UK Collaborative Group on HIV Drug Resistance: Assessment of automated genotyping protocols as tools for surveillance of HIV-1 genetic diversity. *AIDS* 2006, 20: 1521-1529). One of the reasons for the disagreement was attributed to the increasing divergence and complexity caused by recombination. It was also noted that closely related subtypes (B and D) or the subtypes sharing common origin (A and CRF01_AE) showed poor concordance rate among those methods.

The present inventor thinks what lies at the bottom of this problem is that the number of reference sequences per subtype was too small. These methods have used two to four hand-picked reference sequences. Having been carefully chosen by experts among the high-quality whole-genome sequences, they are to cover the diversity of each subtype as much as possible. However, with intrinsically small numbers of references per subtype, they cannot address the confidence of subtype predictions; a low E-value of a pairwise alignment or a high bootstrap value of a phylogenetic tree indicates the reliability of the unit operation, but does not necessarily guarantee a confident subtype classification, as a whole.

Recognition of this issue of lacking a statistical confidence measure, brought about the introduction of STAR, a method based on statistical models of position-specific scoring matrix built from multiple sequence alignment (MSA) of each subtype. However, its current implementation has several limitations: it was applied to HIV-1 amino acid sequences only, based on a small number of references (all together 141 for 11 subtypes), and tested with less than 1,000 sequences.

Recently, new genotyping (or subtyping) methods based on nucleotide composition strings have been introduced. It is unique in that it bypasses the multiple sequence alignment and still achieves high accuracy. However, it also uses only 42 reference sequences and has been tested with 1,156 sequences. Considering the explosive increase in the numbers of these viral sequences, the test cases of these conventional methods were rather small, of ten thousands at most.

Therefore, the object of the present invention is to provide a novel method for classifying genotype or subtype of query sequences which are known to public. It is critical to evaluate how well each subtype population is clustered, before attempting to classify a query sequence. Consider a case where the reference sequences are mostly well segregated by subtype except for two or more subtypes that overlap at least partially: those methods that rely on a few references may not notice this problem and may assign an apparent subtype with a high score. Due to varying mutation rate along the sequence range, the phylogenetic power of each gene segment may also vary. This is particularly critical for relatively short partial sequences. In other words, even the well characterized references that are otherwise distinctively clustered may not be resolved if only part of the sequence region is considered in genotyping (or subtyping).

The nearest neighbor methods do not evaluate this validity of the background classification models, since they concern the alignments of only query-to-reference, not reference-to-reference. REGA, one of the tree-based methods, concerns whether the query is inside or outside the cluster formed by a group of references (de Oliveira T, Deforche K, Cassol S, Salminen M, Paraskevis D, Seebregts C, Snoeck J, van Rensburg E J, Wensing A M, van de Vijver D A, Boucher C A, Camacho R, Vandamme A M: An automated genotyping system for analysis of HIV-1 and other microbial sequences. Bioinformatics 2005, 21: 3797-3800). However, as far as the present inventor knows, no tools report such a measure quantitatively.

Therefore, the present inventor presents a method which develops the background classification models based on the distances among the reference sequences, re-evaluates their validity for each query, and reports the statistical significance of genotype (or subtype) assignment in terms of posterior probabilities.

As such, the method of the present invention is suited for the cases where many reference sequences are available. The present invention achieves such goals by combining principal coordinate analysis (PCoA) with linear discriminant analysis (LDA), both of which are well established statistical tools with popular usages in biological sciences. PCoA, also known as classical multidimensional scaling (MDS), maps the sequences to a high-dimensional principal coordinate space, while trying to preserve the distance relationships among them as much as possible. PCoA has been widely applied to the discovery of global trends in a sequence set, complementing tree-based methods in phylogenetic analysis.

Since subtypes have been defined as distinct monophyletic groups in a phylogenetic tree, each subtype should form a well separated cluster in a MDS space if an appropriately high dimension is chosen. In such cases, a set of hyperplanes that separate these clusters may be found and a query relative to the hyperplanes may be classified. For this purpose, the present invention applies LDA, a straightforward and powerful classification method, to the MDS coordinates and assigns a query to the genotype (or subtype) that shows the highest posterior probability of membership.

This probability can be useful in detecting any ambiguous cases, for which careful examination is required. The method of the present invention tests the LDA models through the leave-one-out cross-validation (LOOCV), which can be used to assess the model validity by examining the misclassification rate. As the sequences are represented by coordinates, a simple measure can be also developed for detecting genotype (or subtype) outliers.

The present inventor has tested the present invention with virtually all the HIV-1 and HCV sequences available from NCBI GenBank (nucleotide) and GenPept (protein).

DISCLOSURE

Technical Problem

The primary object of the present invention is to provide a method for classifying genotype or subtype of query sequence, comprising: (i) selecting base sequences of various viruses of which genotypes or subtypes are known as reference sequences and obtaining a distance matrix by calculating distances between sequences in a multiple alignment of said reference sequences; and (ii) developing a discriminant equation which may classify the reference sequences by performing discriminant analysis for a cluster obtained by clustering said reference sequences through multidimensional scaling of the distance matrix, followed by classifying genotype or subtype of a query sequence according to said discriminant equation.

Technical Solution

The above-mentioned primary object of the present invention can be achieved by providing a method for classifying genotype or subtype of query sequence, comprising: (i) selecting base sequences of various viruses of which genotypes or subtypes are known as reference sequences and obtaining a distance matrix by calculating distances between sequences in a multiple alignment of said reference sequences; and (ii) developing a discriminant equation which may classify the reference sequences by performing discriminant analysis for a cluster obtained by clustering said reference sequences through multidimensional scaling of the distance matrix, followed by classifying genotype or subtype of a query sequence according to said discriminant equation.

The step (i) of the method of the present invention may further comprise removing indels from said multiple alignment.

In addition, the multidimensional scaling of the step (ii) of the method of the present invention is preferably a principal coordinate analysis.

Moreover, the discriminant analysis of the step (ii) of the method of the present invention may be selected from various methods such as a linear discriminant analysis, a quadratic discriminant analysis, a nearest neighbor distance method, a support vector machine or linear classifiers.

Advantageous Effects

The method of the present invention may be effectively utilized for classifying accurately genotype or subtype of viruses by analyzing the sequences of rapidly evolving viruses such as HIV-1 and HCV. In addition, the method of the present invention may be applied to both of nucleotide and protein (peptide) sequences.

Moreover, the method of the present invention may be applied to classify individual subjects into population groups based on a distance matrix of polymorphic markers such as SNP.

BRIEF DESCRIPTION OF THE DRAWINGS

FIG. 5 was generated with a kernel density estimation function implemented in the R statistical package. The portions that were filtered out by O>2 were shaded. While significant portion of the dis-concordant cases were filtered, the loss of the concordant cases was minimized.

FIG. 7(*a*) shows an input screen and FIGS. 7(*b*)-(*d*) show the first through the last pages of the output, respectively.

BEST MODE

Hereinafter, the present invention will be described in greater detail with reference to the following examples and drawings. The examples and drawings are given only for illustration of the present invention and not to be limiting the present invention.
Overall Process The method of the present invention starts the process by creating a multiple sequence alignment (MSA) of the query with the reference sequences. Unlike conventional methods, the present invention requires a large number of references, which should be of high quality and with carefully assigned genotypes (or subtypes). Los Alamos National Laboratory (LANL) databases distribute such MSAs of HIV-1 (www.hiv.lanl.gov) and HCV (hcv.lanl.gov) sequences. LANL also provides the subtype information on each sequence in the MSA. A total of 3,591 nucleotide and 3,478 protein sequences were included in the 2007 release of HIV-1 MSAs, while a total of 3,093 nucleotide and 3,077 protein sequences were in HCV MSAs. It should be noted that for some subtypes, more than 100 sequences were found in the MSA, while there were rare subtypes for which only a few reference sequences were included. This imbalance in sample sizes is a serious problem but the present invention proposes rather a heuristic solution that is based on the global variance. For a fair comparison with other methods, the present inventor decided to honor the MSA of reference sequences already available from the public databases by aligning the query to this reference MSA, rather than creating MSA by myself. This has the advantage of saving the execution time, which is crucial for a web server application. The suit of programs, hmmbuild, hmmcalibrate, and hmmalign (hmmer.janelia.org) are used for this step. After removing indels in the MSA using a PERL script, the pairwise distance matrix among these sequences is calculated using distmat of EMBOSS package (emboss.sourceforge.net) with the Jukes-Cantor correction.

Figure 1:
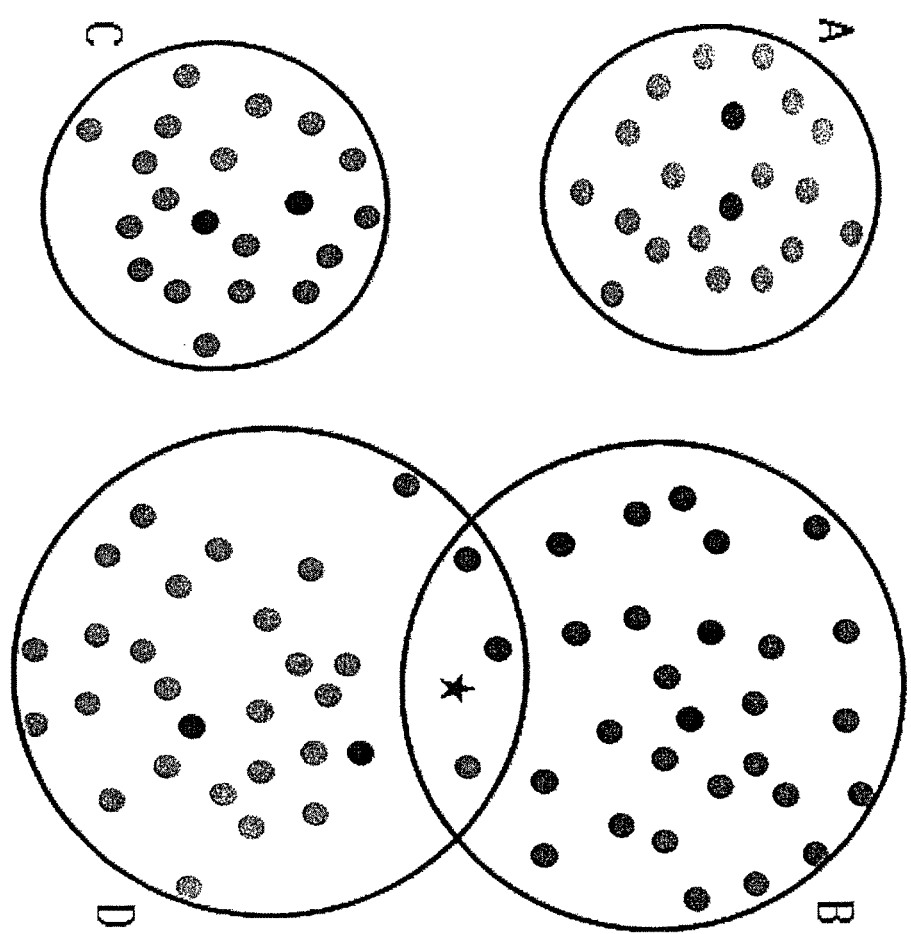
FIG. 1 shows a diagram that represents a method for classifying genotype (or subtype) analysis of viruses, according to the present invention. The spheres represent known sequences clustered into four clusters of A-D, and the interfaces of the groups are represented by a block circle. Solid spheres in each cluster represent reference sequences, respectively, and the query sequence is indicated by star. Since the query sequence is located in the interface between clusters B and D, it is difficult to find out the genotype (or subtype) of the query sequence. On the other hand, the query sequence may be assigned to a nearest neighbor reference sequence by a nearest neighbor method and this case occurs in the cluster D. Depending on the distance to the nearest neighbor reference sequence without considering clustering pattern of the sequences of which classification methods are known, the results may not be robust with respect to selection of the reference sequence.
Figure 2:
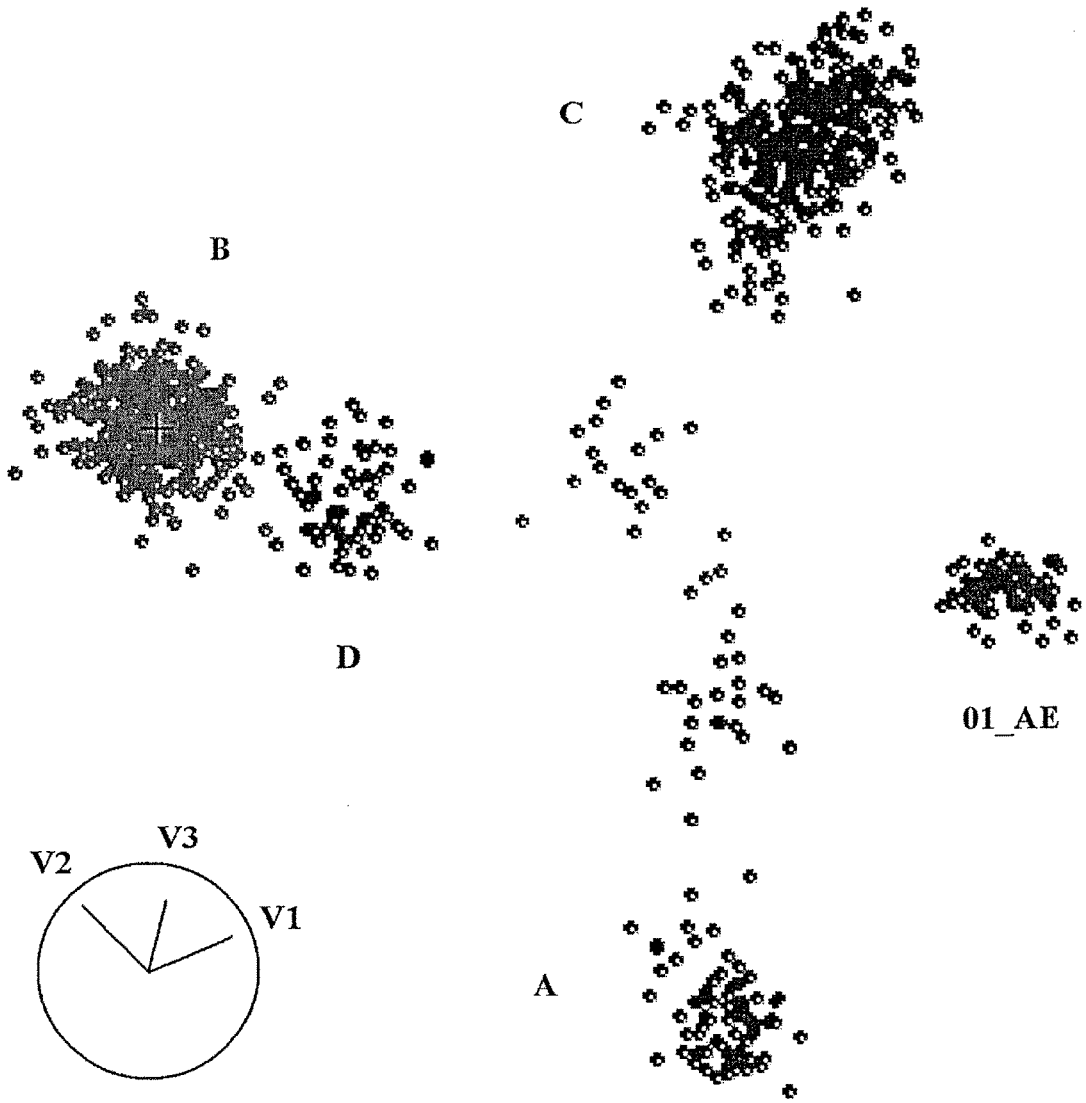
FIG. 2 shows an exemplary MDS plot of HIV-1 sequences along the first (V1), second (V2), and third (V3) principal coordinate axes. The reference sequences were shown as small circles color-coded according to their subtypes. For clarity the subtypes F-K were not labeled. The query was located in the middle of subtype B ('+').

The next step is so-called principal coordinate analysis (PCoA), which turns the distance matrix to a matrix whose components are equivalent to the inner products of the sought coordinates. Through singular value decomposition of the resulting matrix, a set of eigenvectors and associated eigenvalues are obtained up to the specified lower dimensions. The multidimensional coordinates of the sequences whose pairwise Euclidean distances approximate the original distances, are then recovered from a simple matrix operation involving the eigenvectors and eigenvalues. Each eigenvalue is the amount of variance captured along the axis defined by the corresponding eigenvector, also called as the principal coordinate (PC). For convenience, the eigenvalues are sorted in descending order and dimensionality reduction is achieved by taking the top few components. If the within-group variation is negligible, the number of top PCs or the MDS dimensionality, k, should be at most N−1, where N is the number of reference groups. However, depending on the sequence region considered, a subtype might show a complex clustering pattern, splitting into more than one cluster such as sub-subtypes. Consequently, the present inventor took an empirical approach that surveyed the cross-validation error of the reference sequences for k ranging from 1 to 50. This step is implemented with cmdscale in the R statistical system (www.r-project.org) (FIG. 2 shows an exemplary plot of the MDS result). Then, the next step of the present invention is to develop the discriminant models that best classify the references according to their subtypes and assign the subtype membership to the query according to the models. Here, one can envisage applying various classification methods such as K-Nearest Neighbor (K-NN), Support Vector Machine (SVM), and linear classifiers, among others. If this MDS step is really effective, the references should be well clustered according to their subtype membership, and thus the simplest methods such as linear discriminant analysis (LDA) or quadratic discriminant analysis (QDA) should work. Both of them work by fitting a Gaussian distribution function to each group center, while the difference between them is whether global (LDA) or group (QDA) covariance is used. As it can be expected that the within-group divergences may differ from one group to another, QDA may be better suited. However, the sample size imbalance issue mentioned above prevents applying QDA as it becomes unstable with a small number of references for some genotypes (or subtypes). On the other hand, LDA applies the global covariance commonly to all the subtypes and thus may be more robust to this issue. Although it is not as rigorous as QDA, this heuristic approach works reasonably well as long as the group divergences are not too different from one to another. Once the linear discriminants are calculated based on the reference sequences, the posterior probability of belonging to a particular group is given as a function of so-called Mahalanobis distance from the query to the group center. To the query, the maximum a posteriori (MAP) estimate, that is, the subtype having the maximum probability is then assigned. The posterior probability is scaled by the prior that is proportional to the number of references for each subtype. This step is implemented with lda of MASS package in the R statistical system (www.r-project.org).

Cross-Validation of the Prediction Models

The validity of the linear discriminant models are assessed by LOOCV of the genotype (or subtype) membership of the reference sequences. For each one of the references, its genotype (or subtype) is predicted by the models generated from the rest of the references. The misclassification error rate, which is the ratio of the number of misclassified references to the total number of references participated in the validation, is a sensitive measure of the background classification power. Many viral sequences in the public databases are not of the whole genome but cover only a few genes or a part of a gene, and thus their phylogenetic signal may be variable. Consequently, the present inventor re-evaluated the classification power of each prediction using LOOCV. If the reference sequences are not well resolved in the MDS space for a given query, it would be evident in LOOCV, resulting in a high misclassification rate.

Outlier Detection

Even if the references are well separated by subtypes with a low LOOCV error rate, it might be possible that the query sequence itself is abnormal: it could be a composite of two or more subtypes, located in the middle of several subtypes (a recombinant case); it might be close to only one subtype cluster (having a P value close to 1 for that subtype) but far outside the cluster periphery (a divergent case). In the field of multivariate analysis, it is customary to detect outliers by calculating Mahalanobis distance from the sample center and by comparing it with a chi-square distribution. As the Mahalanobis distances have already been incorporated into the calculation of the LDA posterior probability, the present inventor proposes a measure somewhat distinct, namely, outlierness, O, which is the Euclidian distance from the query to the cluster center relative to the maximum divergence of the references belonging to that subtype along that direction:

$$O = \frac{|X_Q - X_C|^2}{\max_{R \in S}[(X_B - X_C), (X_Q - X_C)]}$$ (Eq. 1)

where $X_Q$, $X_R$, and $X_C$ are the MDS vectors of the query, one of the references, and the center of the reference group, S, respectively. The group, S, contains all the reference sequences belonging to the genotype (or subtype) to which the query has been classified. If O is smaller than 1.0, the query is well inside the cluster, and outside otherwise. The present inventor developed a simple heuristic filter based on this: for example, a threshold can be set at 2.0 in order to tolerate some divergence. REGA also implemented an outlier detection scheme by examining the tree topology to see whether the query is within or outside the cluster formed by a group of reference sequences.

Nested Analysis for Recombinant Detection

The standard procedure for characterizing recombinant viral strains includes bootscanning along the sequence in order to locate the recombination spot. It is applicable to long sequences only and takes too much time to be served practically through web for a tool, such as the method of the present invention, that relies on large sample sizes unless a cluster farm having several hundred CPUs is employed. Rather than performing bootscanning, the present inventor addressed the recombination issue by the following approaches: (a) predicting subtypes gene by gene for a query that encompass more than one gene; (b) re-iteration of the analysis in a 'nested' fashion that includes recombinant reference sequences.

HIV-1 and HCV contains an order of 10 genes and, thus, gene by gene analysis of a whole genome sequence may not take 10 times longer than a single gene analysis. If different subtypes are assigned with high confidences to different gene components of a query, it may hint a recombinant case. For some recombinants, the breakpoint may occur in the middle of a gene. In such cases, it is likely that the posterior probability of classification is not dominated by just one subtype but the second or so would have a non-negligible P value. The present inventor re-iterated the prediction process in a 'nested' fashion by focusing on the subtypes having the P value greater than 0.01 and the associated recombinant subtypes. For example, the references include CRF02_AG group if the P value of either A or G group is greater than 0.01.

Web Server Development

Figure 7D:
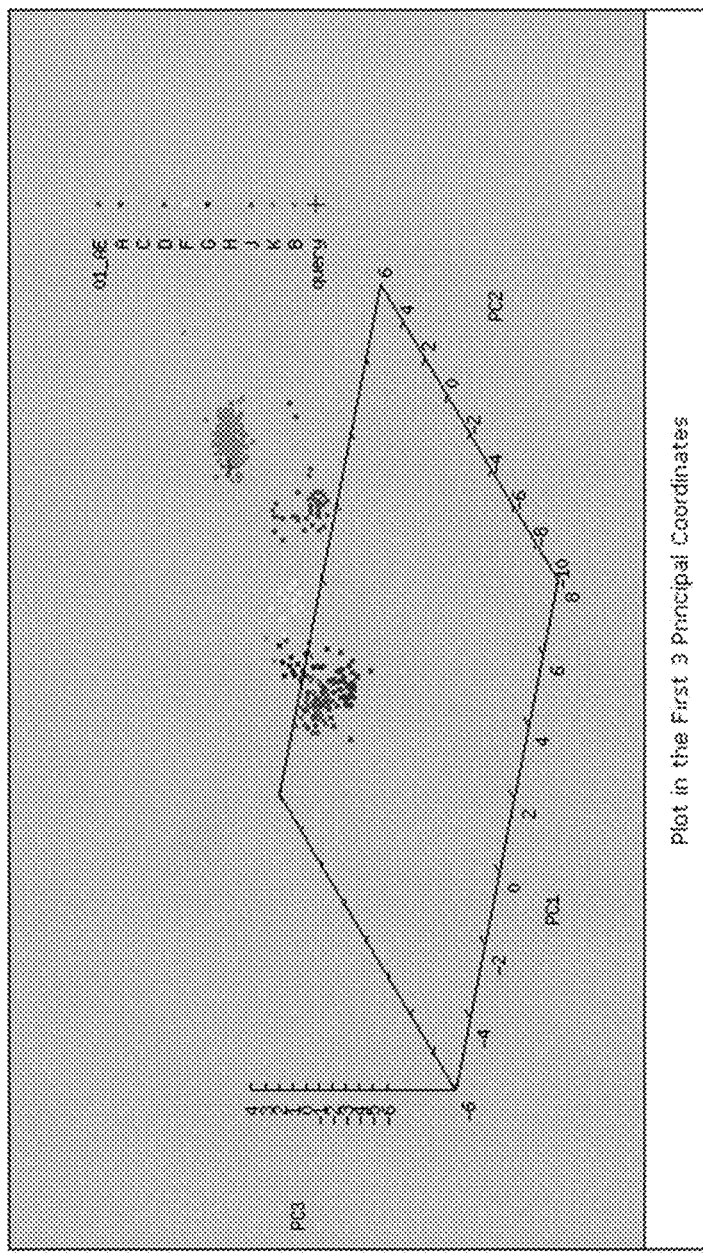
FIG. 7 shows screenshots of web server for the present invention for subtyping HIV-1 sequences.
Figure 8A:
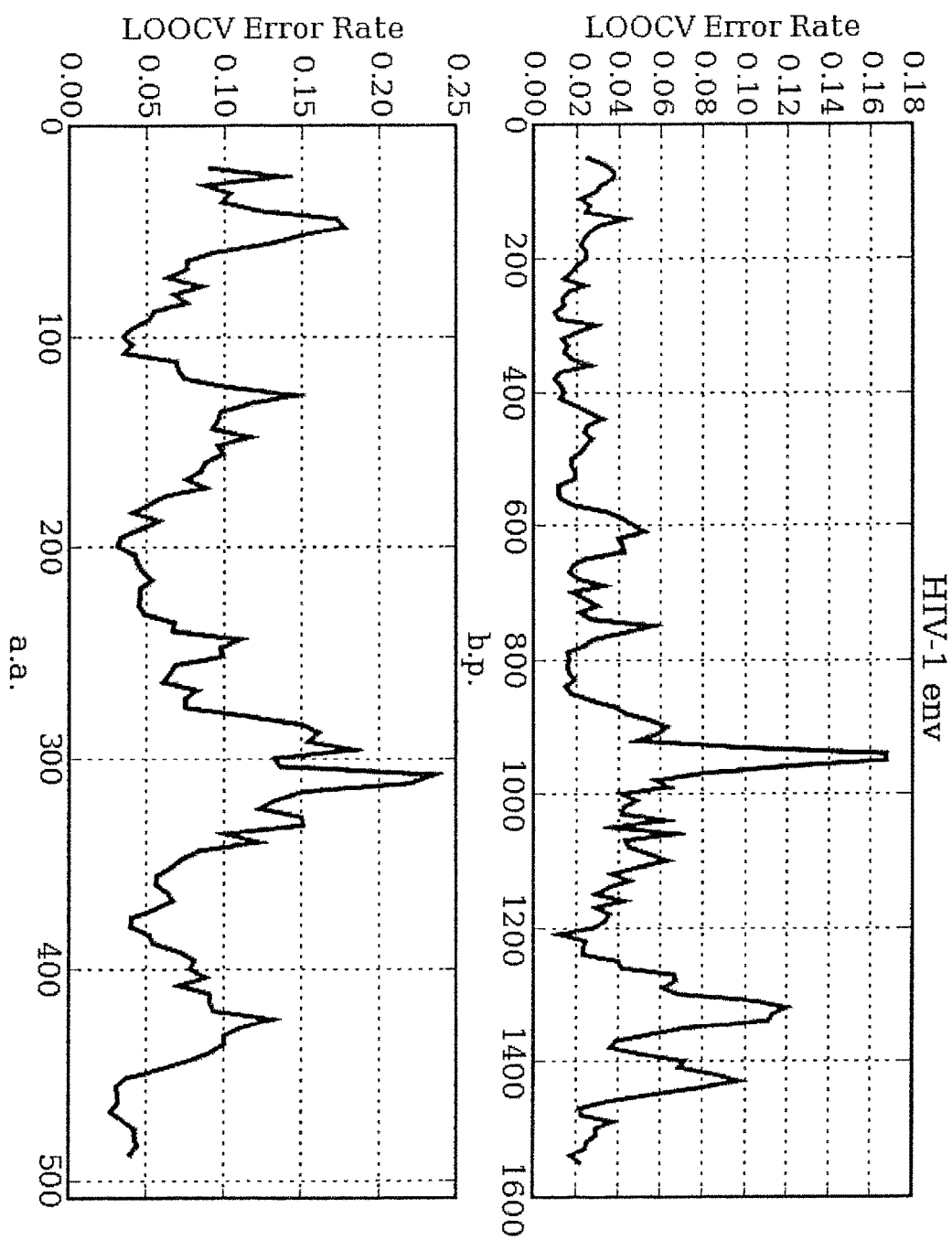
FIG. 8 shows LOOCV error rates in sliding windows for HIV-1 nucleotide (upper panel) and protein (lower panel) sequences ((a) env, (b) gag, (c) nef, (d) pol, (e) vif, (f) vpu).
Figure 8B:
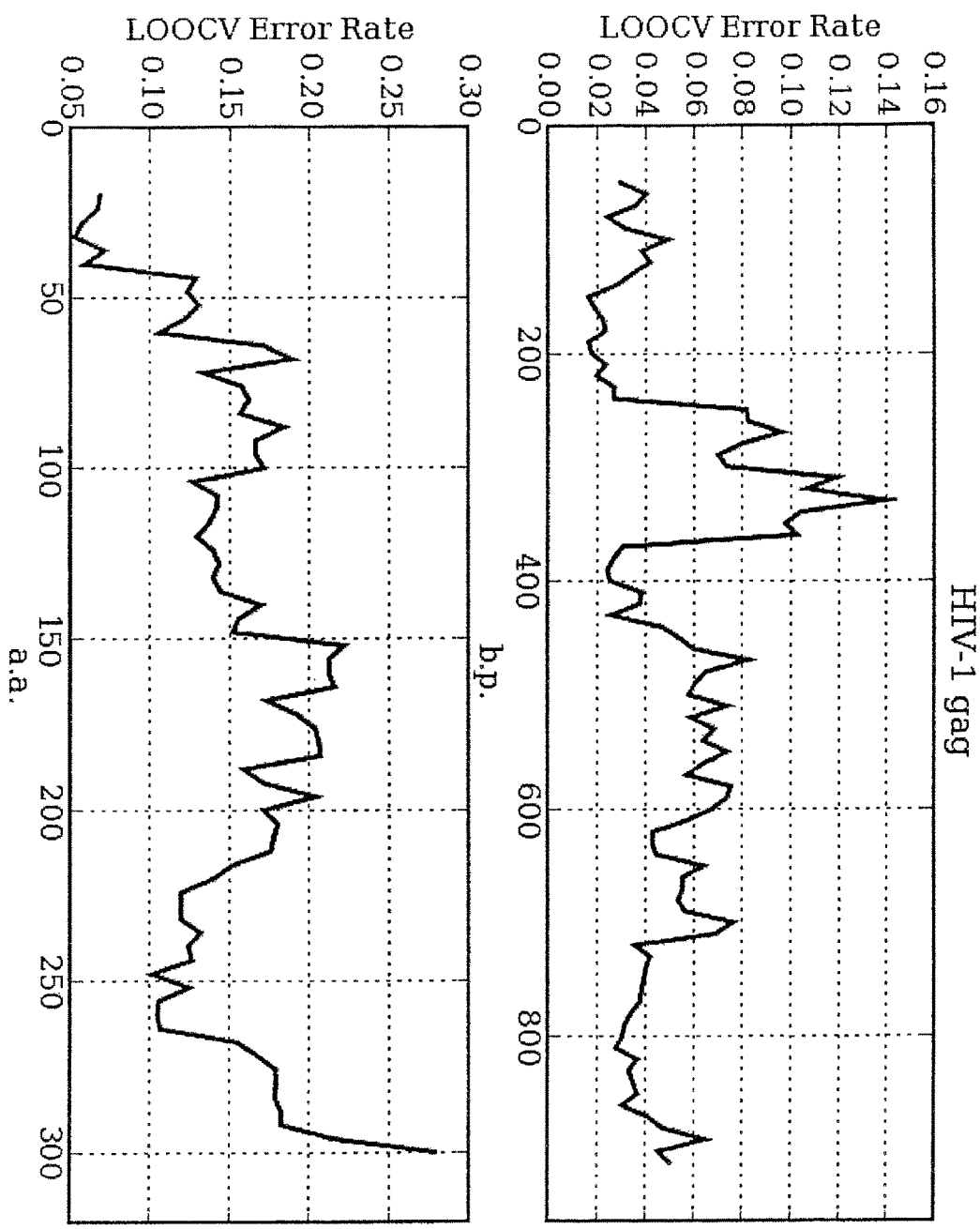
Figure 8C:
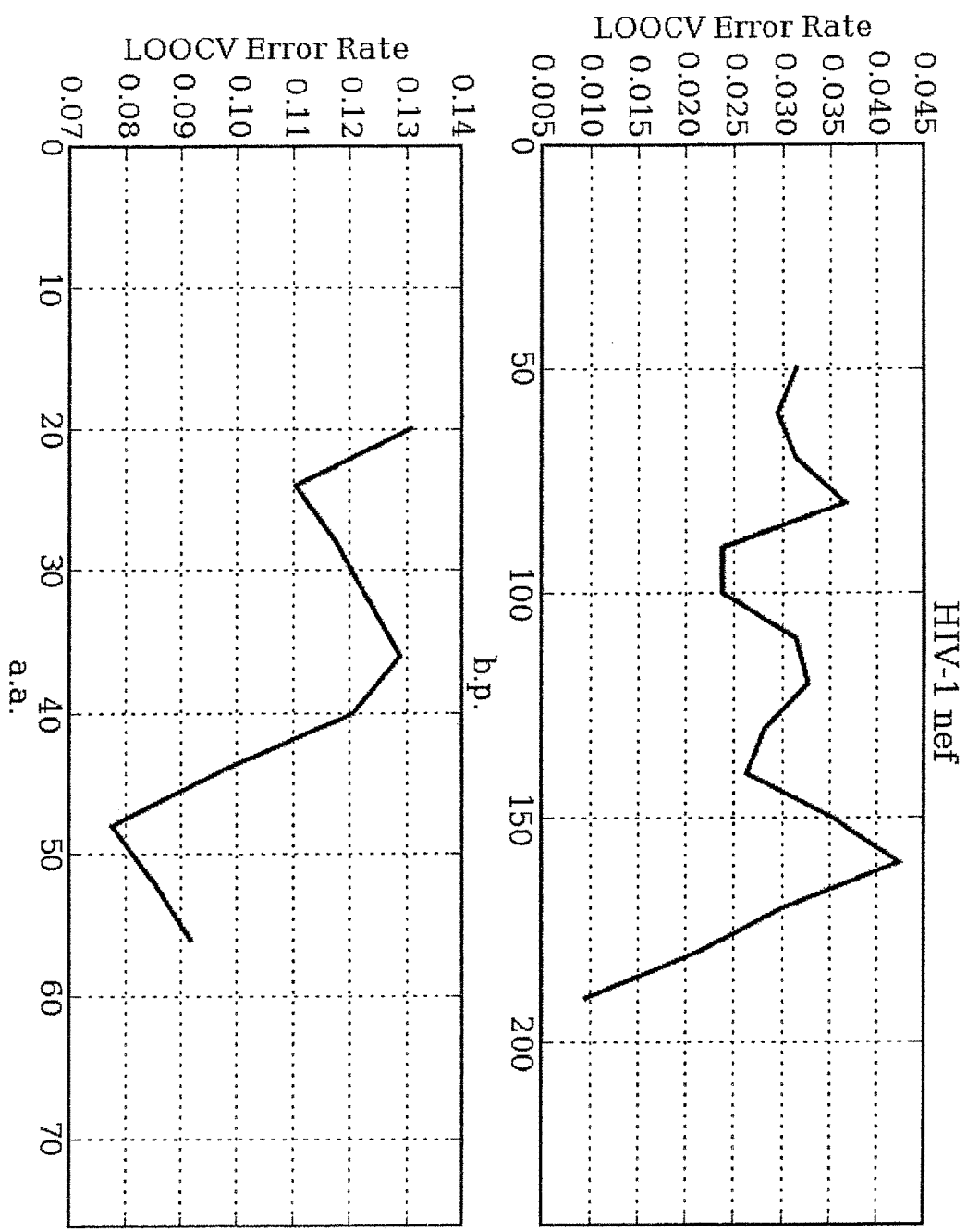
Figure 8D:
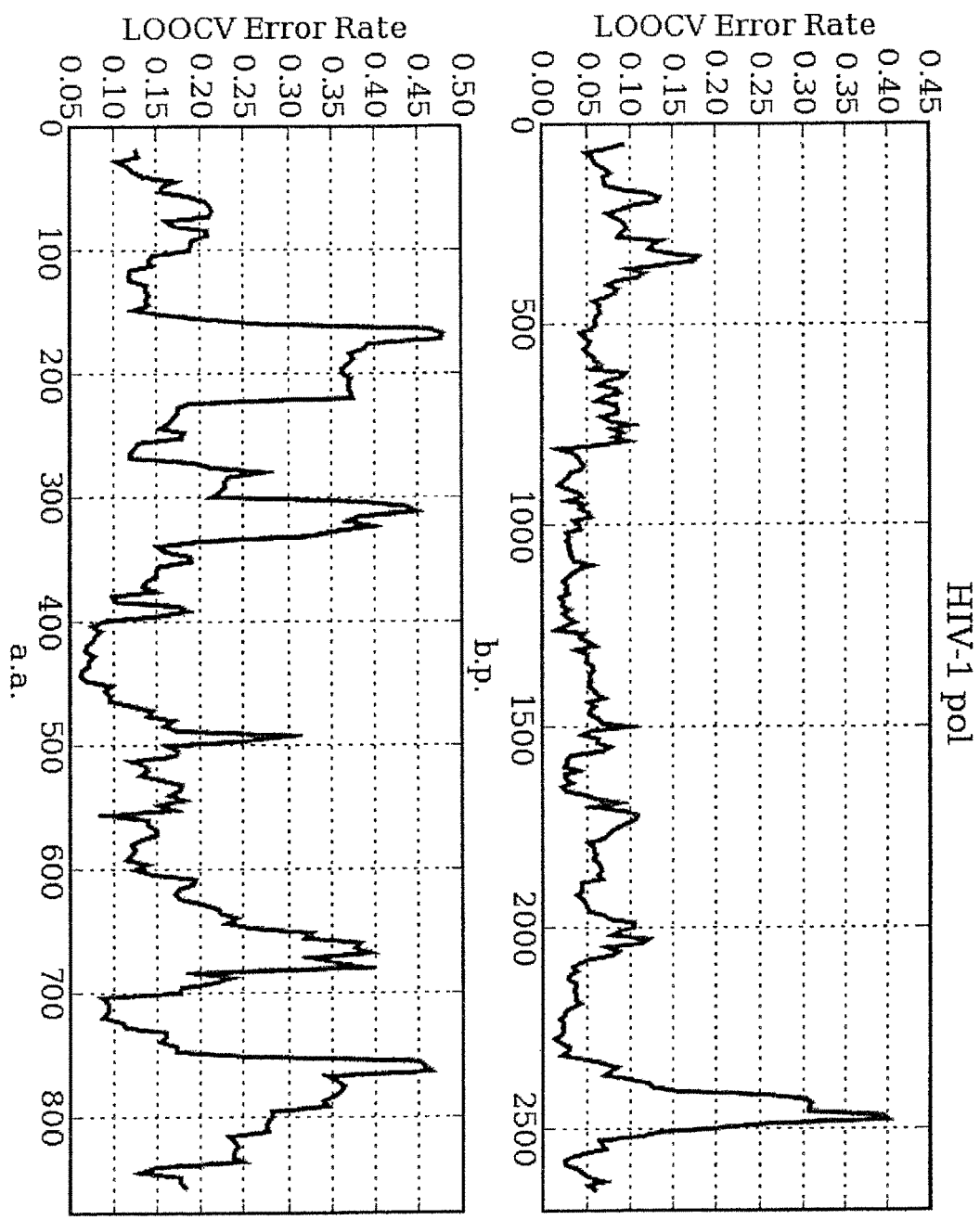
Figure 8E:
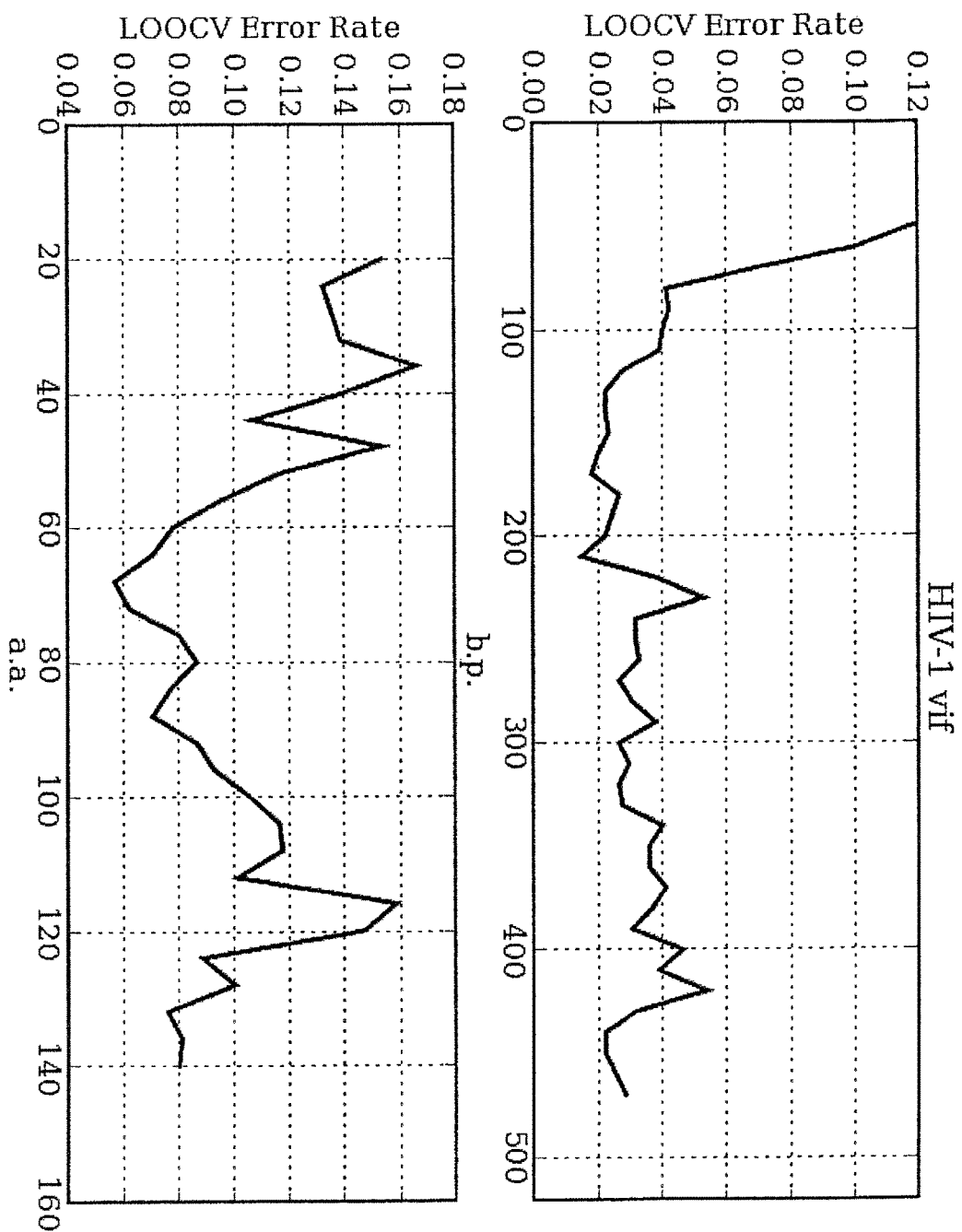
Figure 8F:
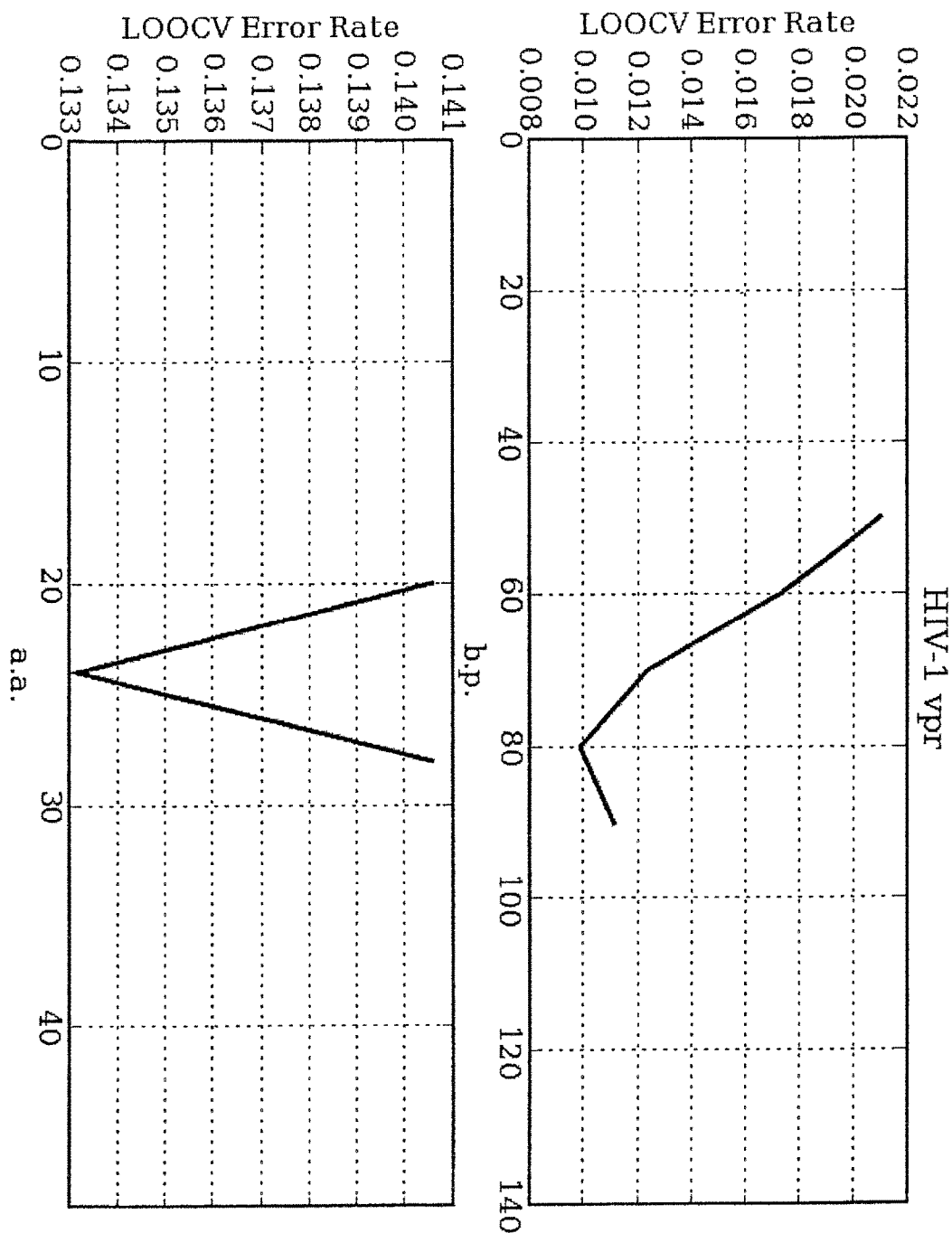
Figure 9A:
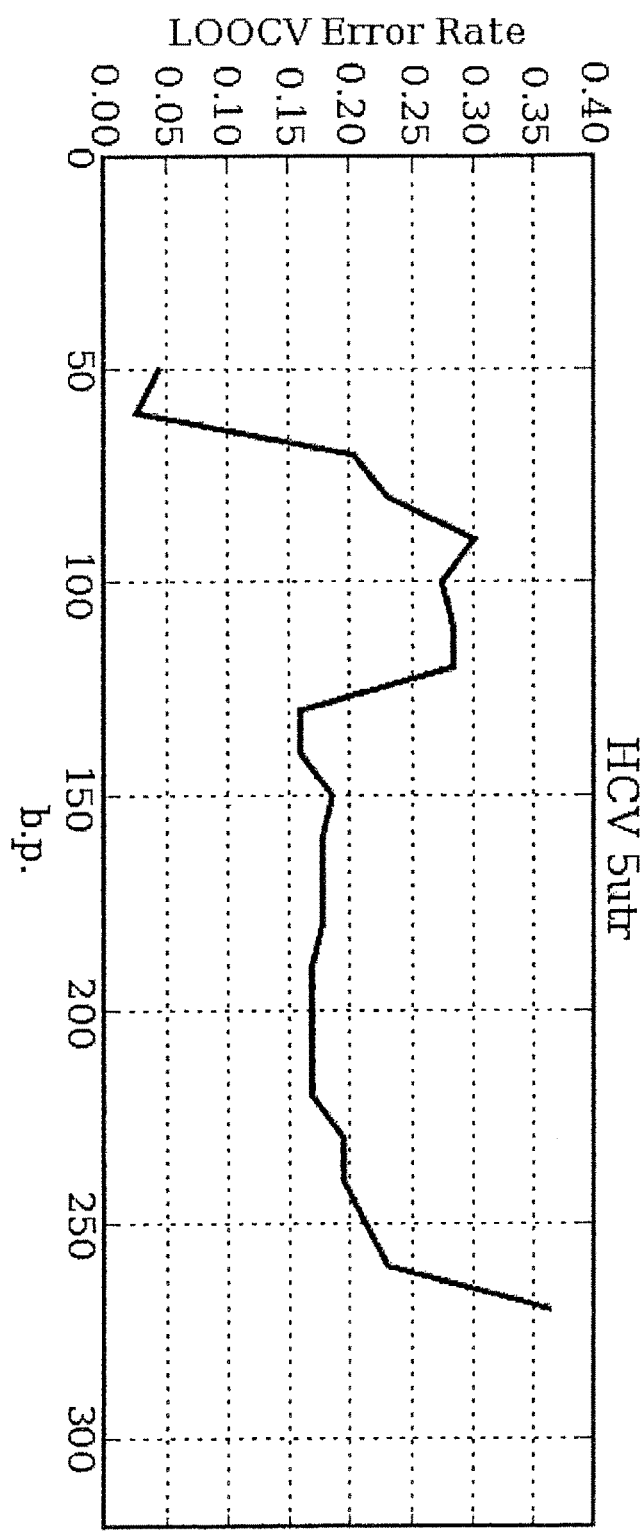
FIG. 9 shows LOOCV error rates in sliding windows for HCV nucleotide (upper panel) and protein (lower panel) sequences ((a) utr, (b) arfp, (c) core, (d) e1, (e) e2, (f) ns2, (g) ns3, (h) ns4a, (i) ns4b, (j) ns5a, (k) ns5b, (l) okamoto, (m) p7).
Figure 9B:
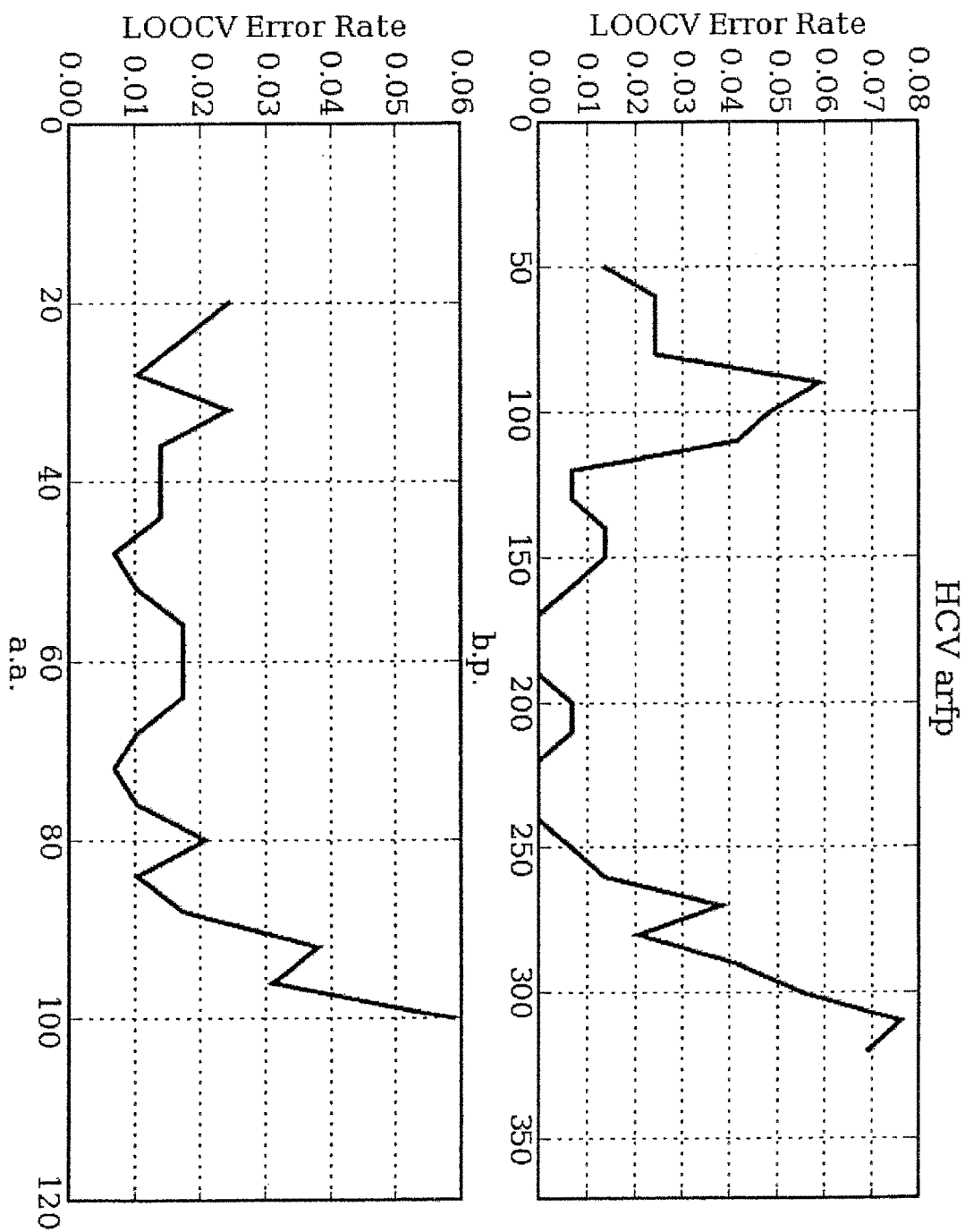
Figure 9C:
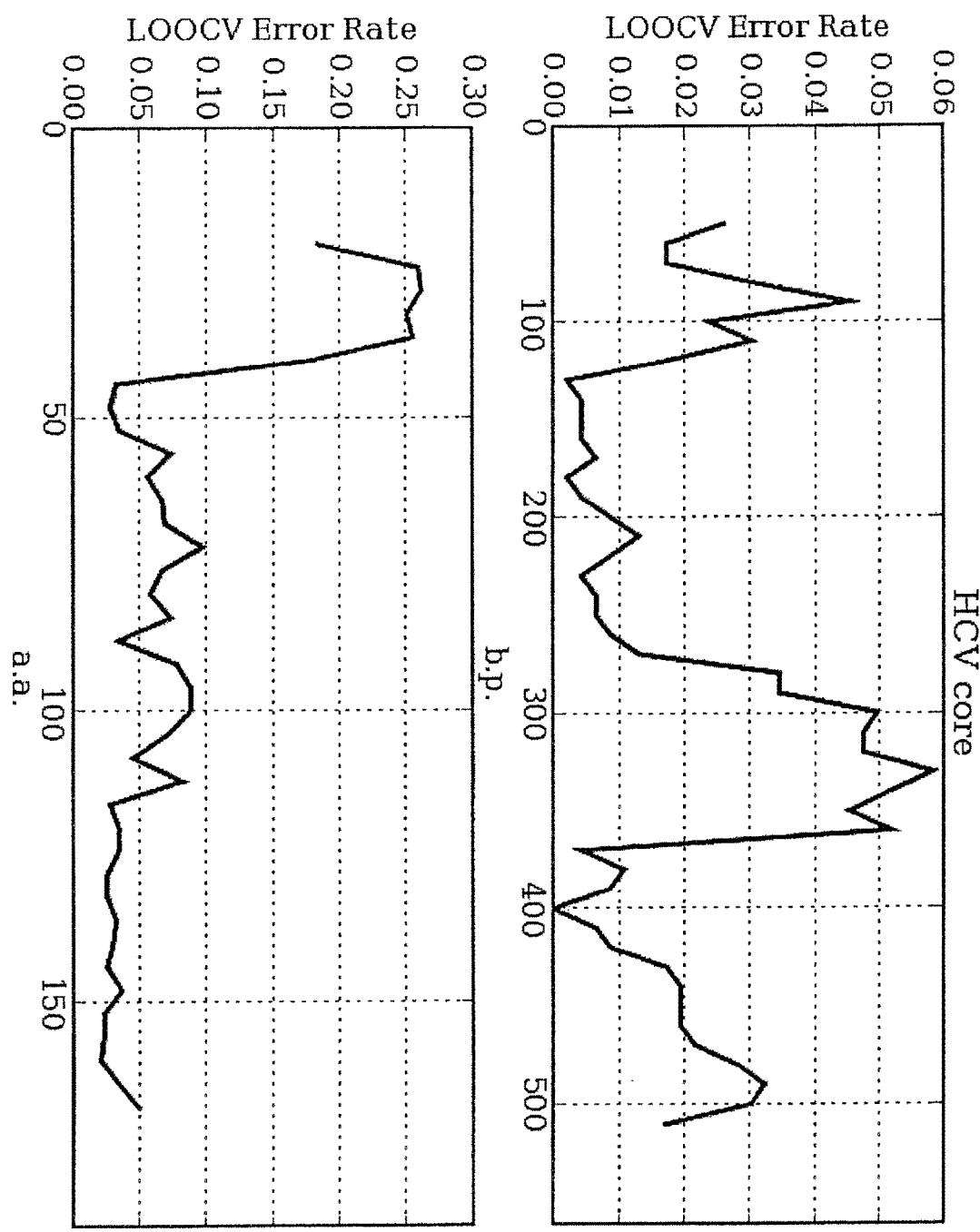
Figure 9D:
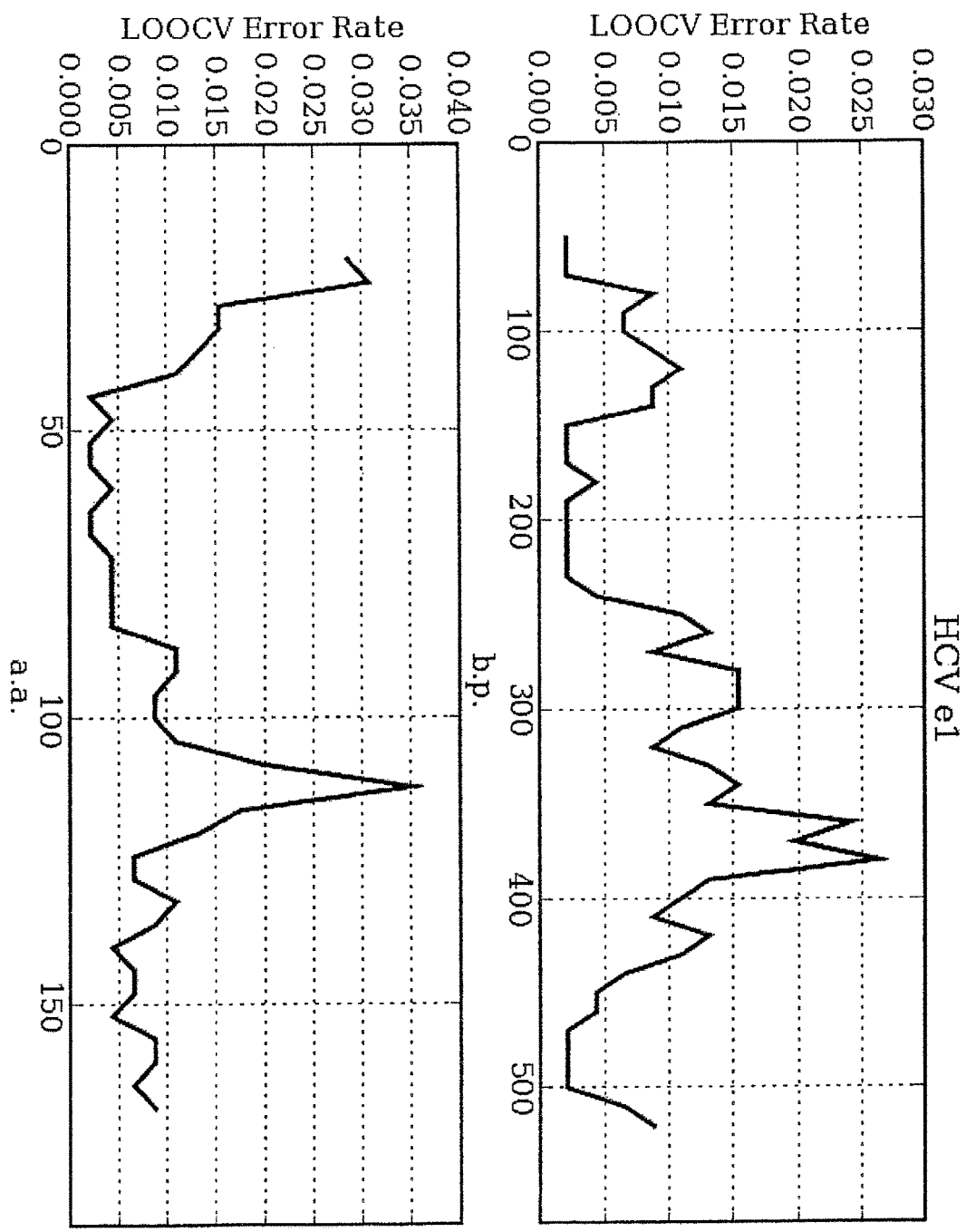
Figure 9E:
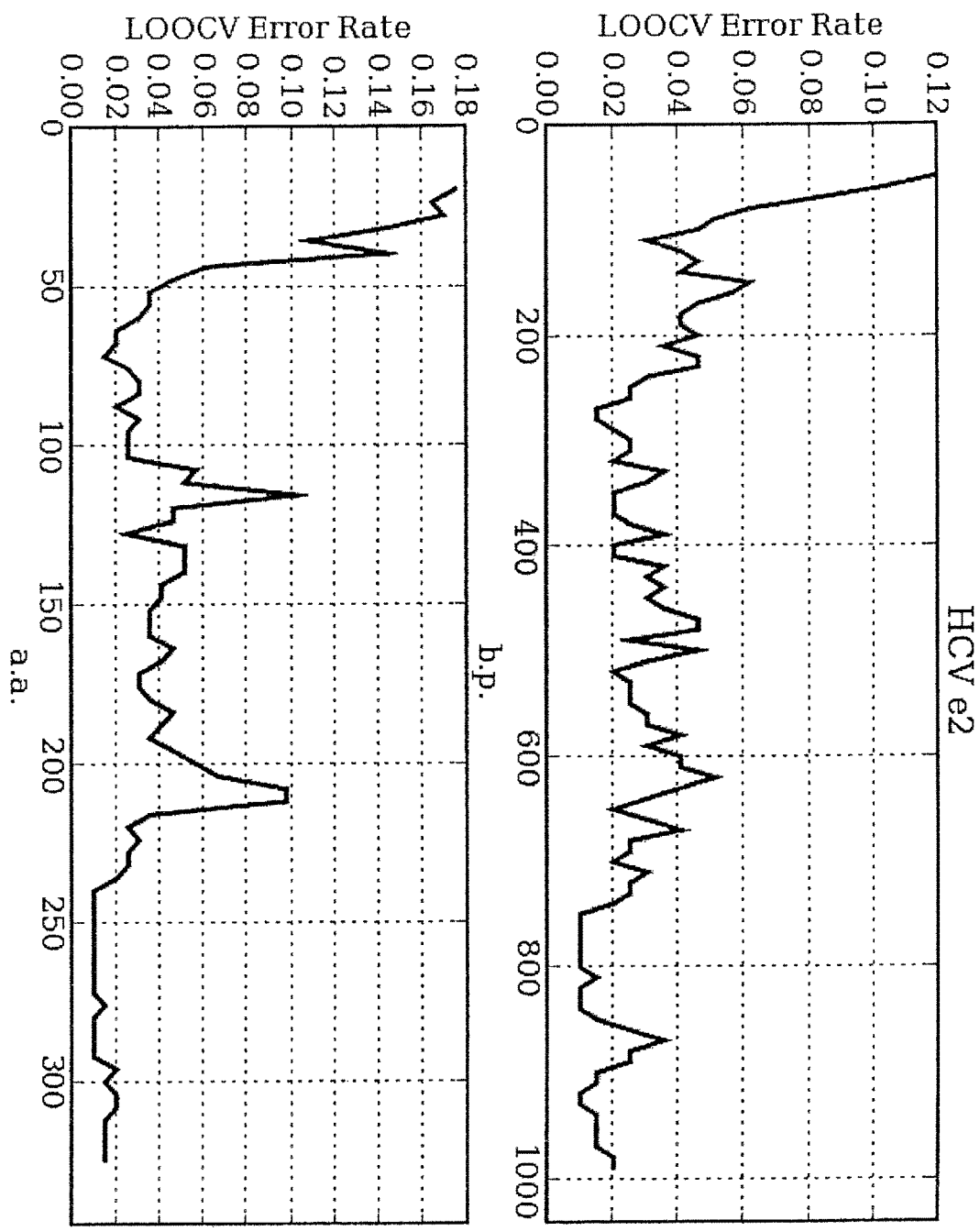
Figure 9G:
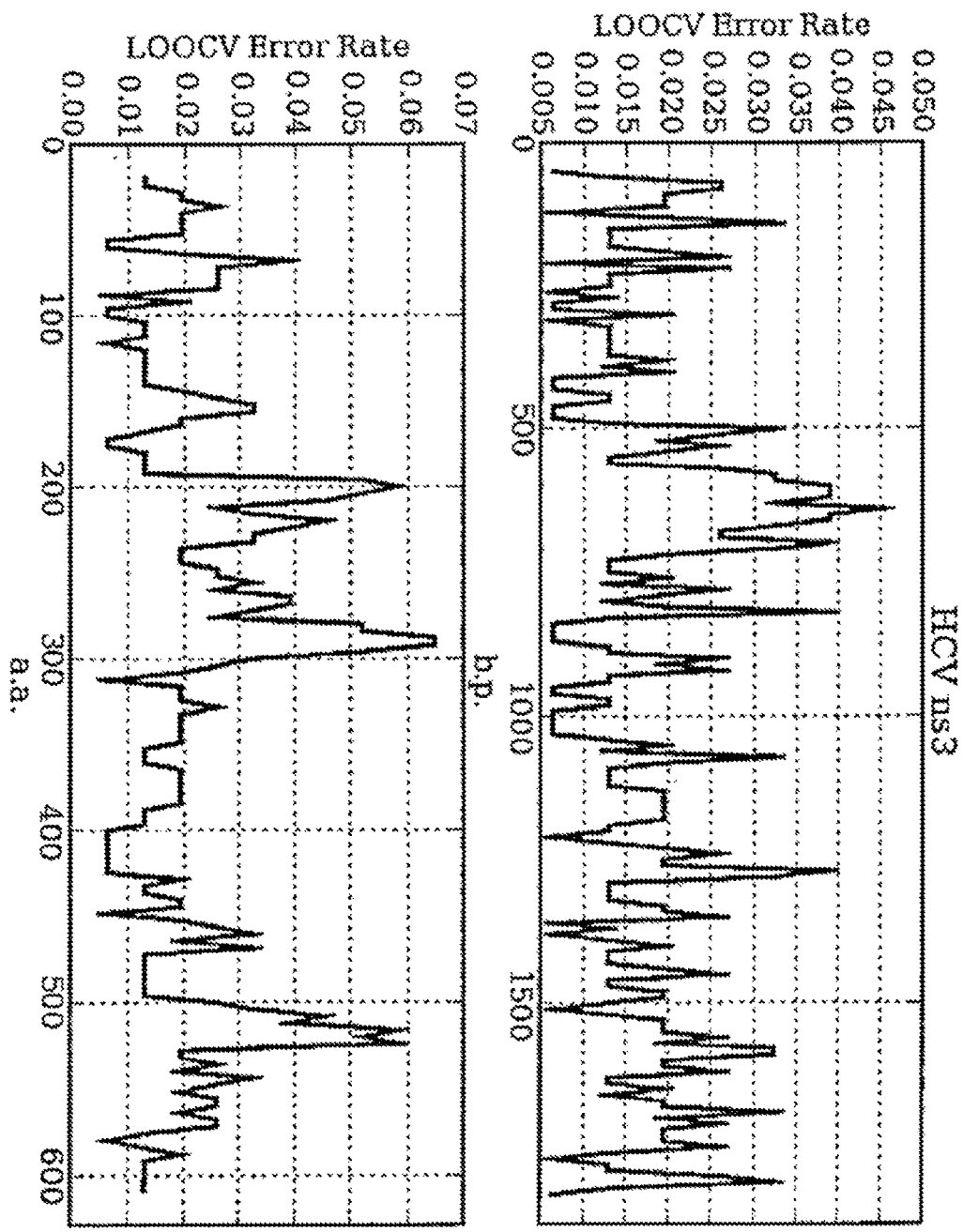
Figure 9H:
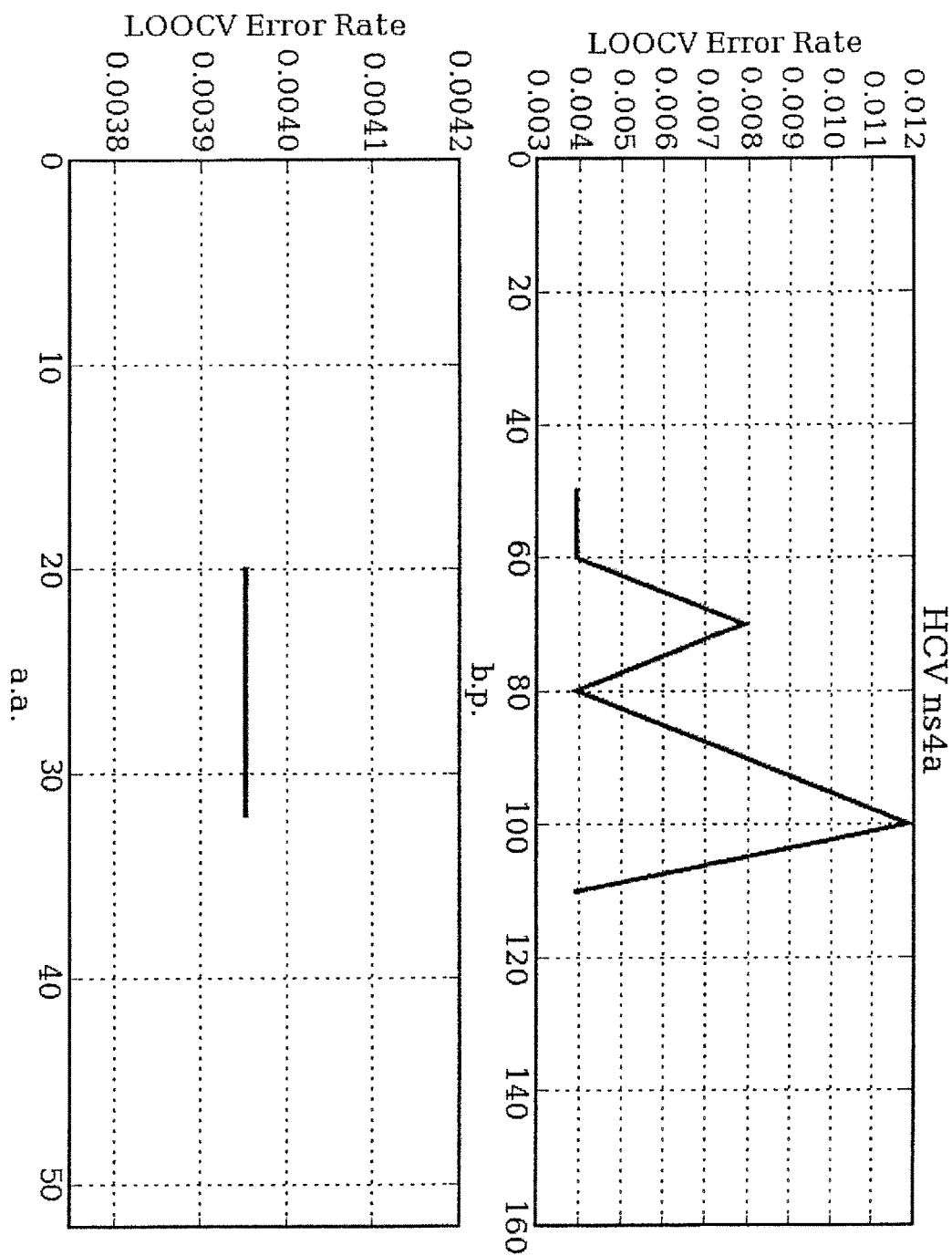
Figure 9I:
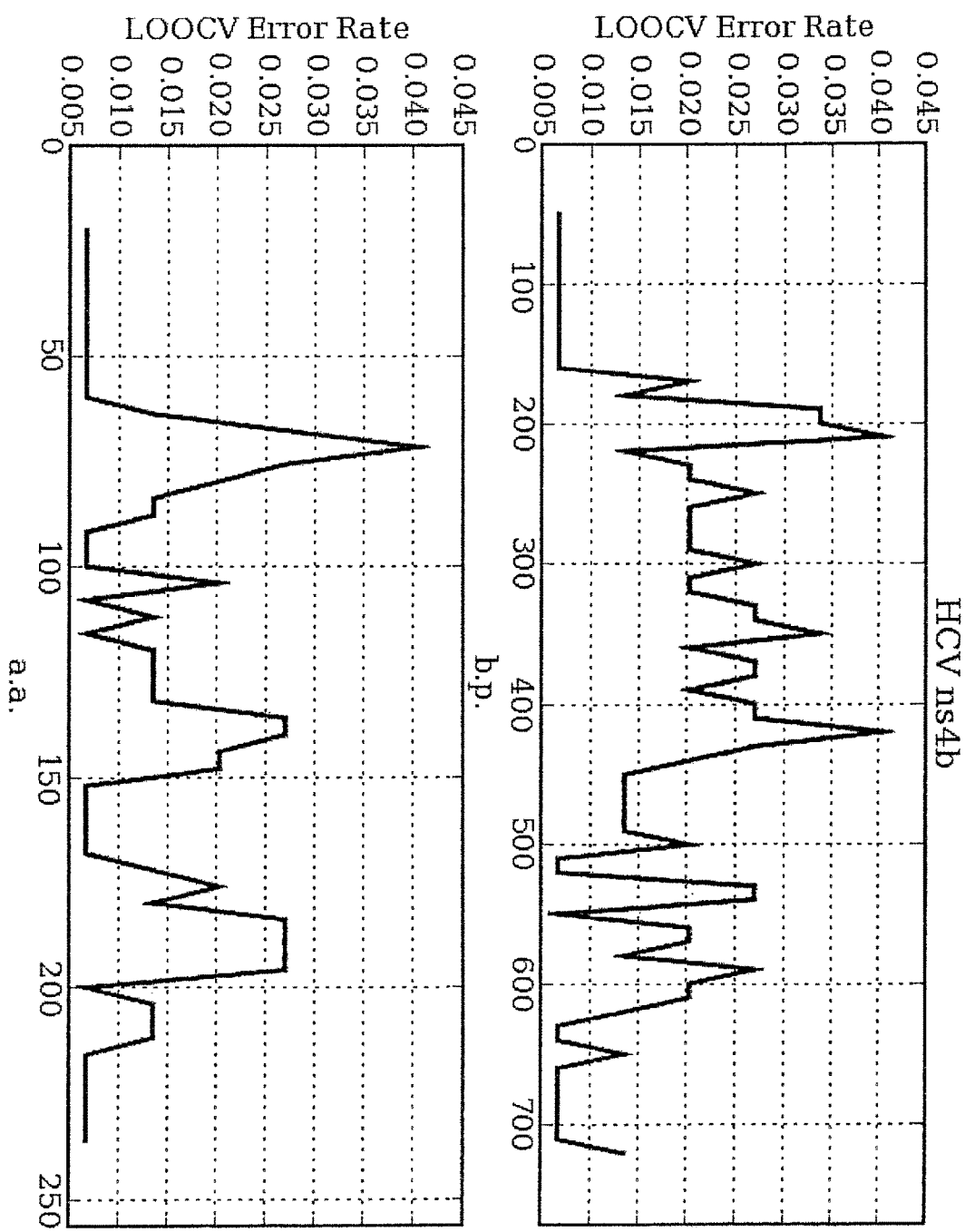
Figure 9J:
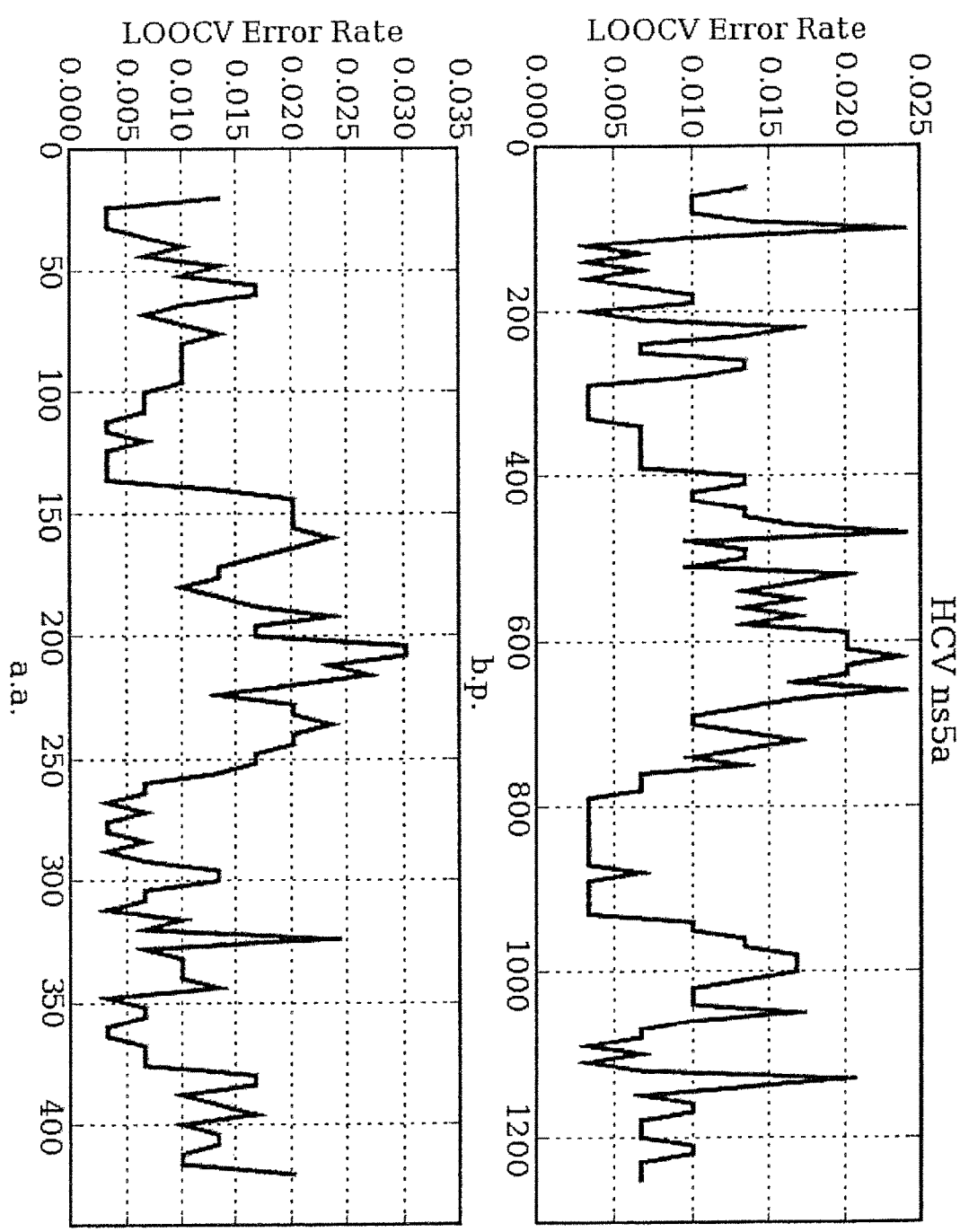
Figure 9K:
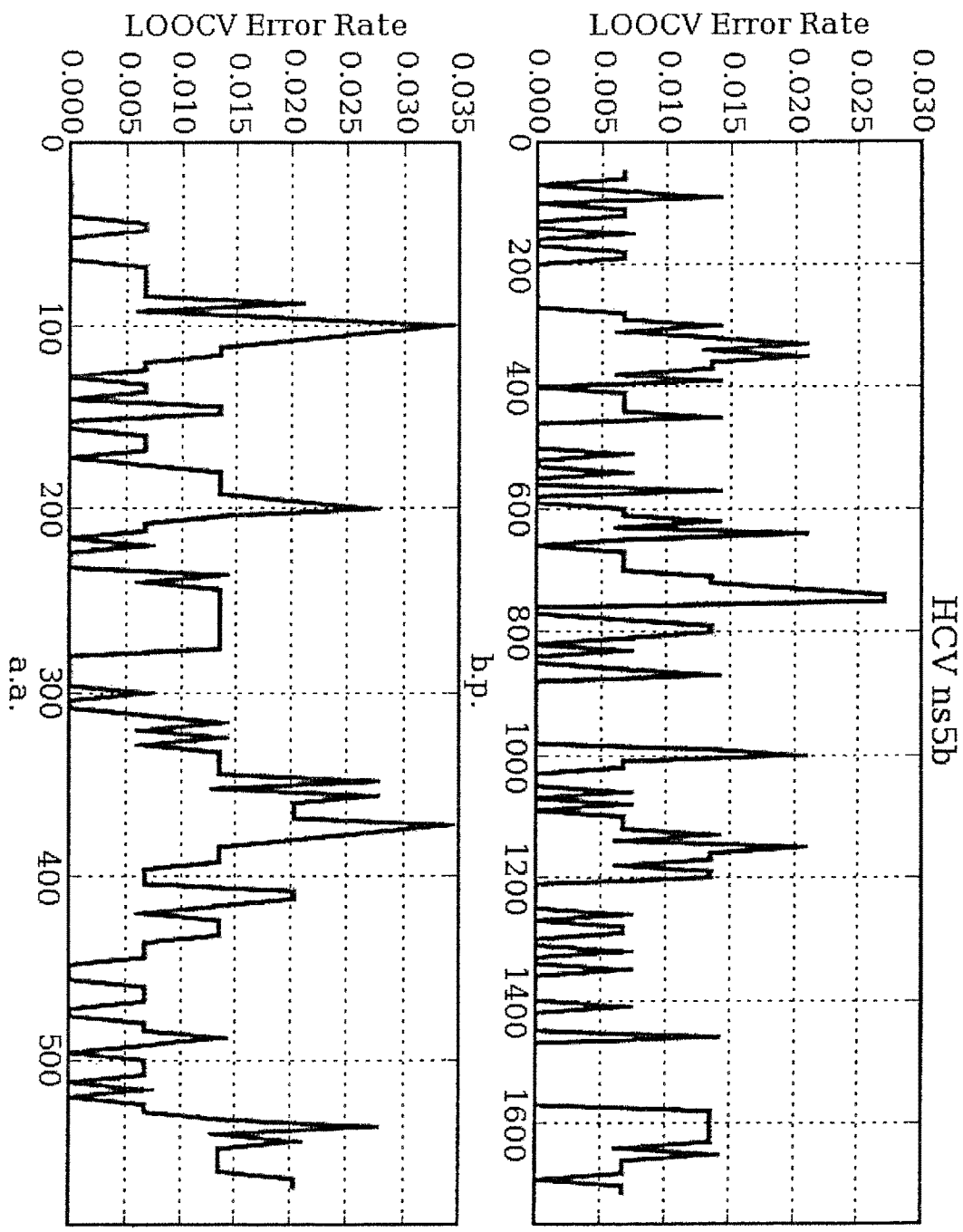
Figure 9I:
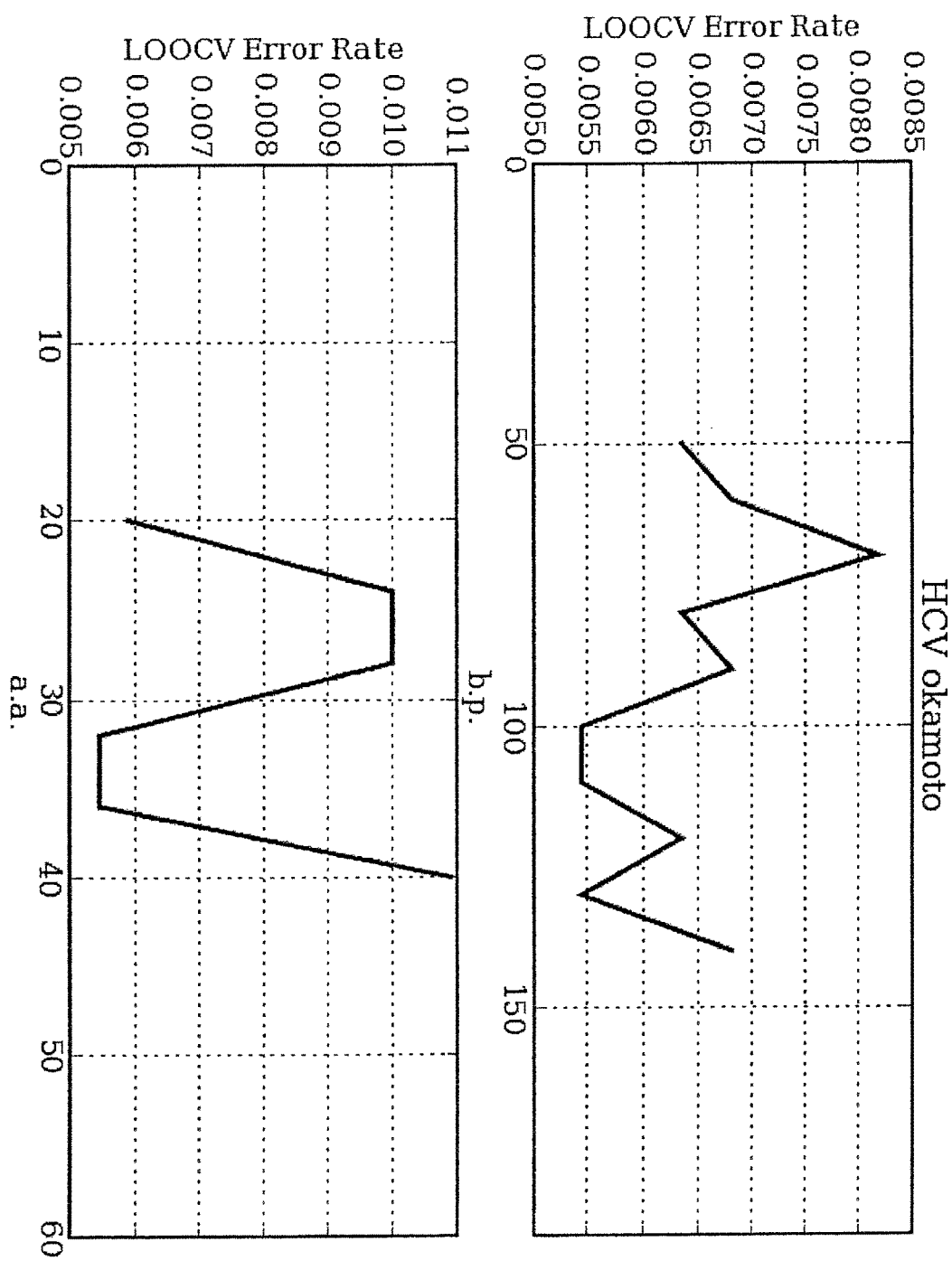

Apache web servers that accept a nucleotide sequence as a query and predict the genotype (or subtype) for each gene segment of the query have been developed, one for each of HIV-1 and HCV. The corresponding protein-versions that accept an amino acid sequence as a query have also been developed. These are freely accessible at www.muldas.org/MuLDAS. Each CGI program written in PERL wraps the component programs that have been downloaded from the respective distribution web sites of HMMER, EMBOSS, and R. Since the calculation of distance matrix consumes much of the run time, the present inventor split the task into several, typically four, computational nodes, each of which calculates parts of the rows in parallel, and the results are integrated by the master node. A typical subtype prediction of a 1000-bp HIV-1 nucleotide sequence took around 20 seconds on an Intel Xeon CPU Linux box. The web servers reported the MAP genotype (or subtype) of the query as well as the posterior P for each subtype, the leave-one-out cross-validation result of the prediction models, and the outlier detection result (FIG. 7 for screenshots). The 3D plot of the query and the references in the top three PCs are given in PNG format and an XML file describing all the PCs of the query and the references can be downloaded for a subsequent dynamic interactive visualization with GGobi (www.ggobi.org) (FIG. 2). This is particularly useful for visually examining the quality of clustering and for confirming the outlier detection result that may lead to the discernment of potential new types or recombinants. For HIV-1, the 'nested' analysis as described above was re-iterated and the result was reported as well.

The web site also operates database servers that store the pre-calculated results of HIV-1 subtypes and HCV genotypes, which are predicted by the identical method as the prediction servers. All the new entries of HIV-1 or HCV sequences in NCBI GenBank and GenPept are downloaded regularly, typically daily, and their genotypes (or subtypes) are predicted and stored in the databases. The results can be retrieved by either NCBI GI numbers or primary accessions. It is also possible to query the entries by the properties calculated by the system such as posterior probability, LOOCV rate, outlierness, genotype (or subtype), or gene segment. The retrieved result includes the genotype (or subtype) information fetched from LANL databases, if any.

Results

The method of the present invention was tested with the sequence datasets of HIV-1 and HCV downloaded from NCBI GenBank and GenPept. The subtype information of nucleotide sequences were retrieved from the LANL website for 158,834 HIV-1 (including 8,832 recombinants) and 48,720 HCV sequences (non-recombinants only) that have not been used as reference sequences, and were used to trace out the subtype information of protein sequences which originate from the nucleotide sequence. For some of the sequences, the genotypes/subtypes were given by the original submitters and otherwise they were assigned by LANL.

Genotype (or Subtype) Nomenclatures of the Test Datasets

HIV-1 sequences were grouped into M (main), N (non-main), U (unclassified) and O (outgroup) groups. Most of the sequences available belong to M group. As N and O groups are quite distant from M group, the subtypes of M group cannot be well resolved in the MDS plot that includes these remote groups. Consequently, the present inventor focused on classifying M group sequences into subtypes, A-D, F-H, J, and K. Among M group subtypes, A and F are sometimes further split into sub-subtypes, A1 and A2, and F1 and F2, respectively.

However, some new sequences were still being reported at the subtype level in the LANL database. This was the case even to the sequences included in MSA produced by LANL.

Resolving sub-subtypes for relatively short sequences using the present invention requires a 'nested' analysis using the relevant subtype sequences only. Due to these reasons, the present inventor did not attempt to distinguish sub-subtypes and classified them at the subtype level. Different subtypes of the M group sequences can recombine to form a new strain.

If these strains were found in more than three epidemiologically independent patients, they are called circulating recombinant forms (CRFs). Among the CRFs, CRF01_AE was formed by recombination of A and now extinct E strains, and constitutes a large family that is distinct from A subtype.

The M group and CRF01_AE subtypes have been called as the 'major' subtypes and the method of the present invention was performed against them as the 'major' analysis. Table 1 lists the breakdown of the statistics by subtypes and gene segments of all the test sequences that have been classified to the 'major' groups by LANL (refer to Table 2 for the corresponding protein sequences). The distribution was far from uniform, representing study biases: sequences belonged to subtypes H, J, and K were rare; especially for auxiliary proteins such as vif and vpr, non-B strains were too rare to evaluate the classification accuracy.

TABLE 1

Summary statistics of the benchmark test for HIV-1 M group and CRF01_AE nucleotide sequences

| | A | B | C | D | F | G | H | J | K | 01_AE | Total |
|---|---|---|---|---|---|---|---|---|---|---|---|
| (a) Number of gene segments per subtype before filtering | | | | | | | | | | | |
| Gene | | | | | | | | | | | |
| gag | 2,465 | 8,576 | 2,455 | 672 | 128 | 406 | 35 | 15 | 11 | 596 | 15,359 |
| pol | 2,897 | 50,595 | 4,590 | 1,076 | 753 | 1,035 | 75 | 58 | 8 | 4,398 | 65,485 |
| vif | 51 | 1,105 | 98 | 28 | 3 | 11 | 0 | 1 | 0 | 106 | 1,403 |
| vpr | 41 | 1,504 | 43 | 13 | 4 | 3 | 0 | 1 | 0 | 106 | 1,715 |
| 5tat | 66 | 2,160 | 199 | 45 | 4 | 3 | 0 | 1 | 0 | 108 | 2,586 |
| vpu | 44 | 1,036 | 155 | 14 | 5 | 12 | 0 | 1 | 0 | 146 | 1,413 |
| env | 7,225 | 47,551 | 5,198 | 1,853 | 415 | 912 | 104 | 47 | 19 | 2,861 | 66,185 |
| nef | 284 | 6,055 | 641 | 77 | 15 | 26 | 3 | 1 | 1 | 191 | 7,294 |
| Total | 13,073 | 118,582 | 13,379 | 3,778 | 1,327 | 2,408 | 217 | 125 | 39 | 8,512 | 161,440 |
| Dist. Acc. | 12,669 | 113,361 | 12,824 | 3,694 | 1,302 | 2,370 | 217 | 118 | 39 | 7,686 | 154,280 |
| (b) Number of gene segments per subtype after outlierness filtering (O < 2.0) | | | | | | | | | | | |
| gag | 2,369 | 8,558 | 2,416 | 657 | 91 | 335 | 5 | 0 | 3 | 574 | 15,008 |
| pol | 2,596 | 49,084 | 4,476 | 1,000 | 509 | 733 | 9 | 2 | 0 | 4,160 | 62,569 |
| vif | 51 | 1,104 | 98 | 24 | 2 | 8 | 0 | 0 | 0 | 106 | 1,393 |
| vpr | 41 | 1,496 | 43 | 13 | 2 | 3 | 0 | 0 | 0 | 106 | 1,704 |
| 5tat | 63 | 2,149 | 199 | 44 | 3 | 3 | 0 | 0 | 0 | 108 | 2,569 |
| vpu | 41 | 1,031 | 155 | 14 | 3 | 12 | 0 | 0 | 0 | 146 | 1,402 |
| env | 7,016 | 47,487 | 5,146 | 1,735 | 320 | 708 | 33 | 12 | 7 | 2,823 | 65,287 |
| nef | 277 | 5,969 | 641 | 71 | 13 | 23 | 3 | 1 | 1 | 187 | 7,186 |
| Total | 12,454 | 116,878 | 13,174 | 3,558 | 943 | 1,825 | 50 | 15 | 11 | 8,210 | 157,118 |
| Dist. Acc. | 12,069 | 111,773 | 12,622 | 3,476 | 926 | 1,792 | 50 | 15 | 11 | 7,393 | 150,127 |
| (c) Subtype prediction concordance (%) with LANL Gold Standard before filtering | | | | | | | | | | | |
| gag | 94.73 | 99.07 | 99.27 | 97.77 | 89.06 | 90.64 | 71.43 | 66.67 | 81.82 | 92.95 | 97.70 |
| pol | 88.44 | 99.15 | 99.08 | 96.19 | 98.41 | 96.91 | 96.00 | 56.90 | 75.00 | 98.25 | 98.47 |
| vif | 100 | 99.37 | 98.98 | 85.71 | 100 | 27.27 | — | 0 | — | 100 | 98.50 |
| vpr | 100 | 99.73 | 95.35 | 100 | 100 | 100 | — | 100 | — | 100 | 99.65 |

TABLE 1-continued

Summary statistics of the benchmark test for HIV-1 M group and CRF01_AE nucleotide sequences

| | A | B | C | D | F | G | H | J | K | 01_AE | Total |
|---|---|---|---|---|---|---|---|---|---|---|---|
| 5tat | 84.85 | 99.68 | 100 | 95.56 | 100 | 100 | — | 0 | — | 100 | 99.23 |
| vpu | 70.45 | 99.90 | 100 | 100 | 80.00 | 100 | — | 100 | — | 100 | 98.94 |
| env | 98.52 | 99.64 | 98.15 | 95.14 | 94.22 | 92.76 | 50.00 | 51.06 | 57.89 | 99.62 | 99.02 |
| nef | 97.89 | 98.35 | 99.69 | 93.51 | 86.67 | 96.15 | 100.00 | 0 | 100 | 99.48 | 98.38 |
| Total | 95.40 | 99.32 | 98.80 | 95.84 | 96.01 | 93.98 | 70.05 | 55.20 | 69.23 | 98.46 | 98.65 |

(d) Subtype prediction concordance (%) with LANL Gold Standard after outlierness filtering (O < 2.0)

| | A | B | C | D | F | G | H | J | K | 01_AE | Total |
|---|---|---|---|---|---|---|---|---|---|---|---|
| gag | 97.89 | 99.15 | 99.54 | 98.02 | 95.60 | 89.55 | 60.00 | — | 66.67 | 93.03 | 98.47 |
| pol | 93.45 | 99.33 | 99.55 | 97.50 | 99.21 | 99.05 | 100 | 0 | — | 98.41 | 99.00 |
| vif | 100 | 99.37 | 98.98 | 100 | 100 | 37.50 | — | — | — | 100 | 99.07 |
| vpr | 100 | 99.73 | 95.35 | 100 | 100 | 100 | — | — | — | 100 | 99.65 |
| 5tat | 85.71 | 99.77 | 100 | 95.45 | 100 | 100 | — | — | — | 100 | 99.38 |
| vpu | 75.61 | 100 | 100 | 100 | 66.67 | 100 | — | — | — | 100 | 99.22 |
| env | 99.26 | 99.67 | 98.70 | 98.73 | 94.06 | 95.20 | 27.27 | 0 | 42.86 | 99.65 | 99.39 |
| nef | 99.64 | 99.56 | 99.69 | 94.37 | 92.31 | 100 | 100 | 0 | 100 | 100 | 99.51 |
| Total | 97.66 | 99.49 | 99.22 | 98.15 | 96.92 | 95.56 | 48.00 | 0 | 54.55 | 98.59 | 99.15 |

(e) Confusion table (LANL on the left, the present invention at the top)

| LANL | A | B | C | D | F | G | H | J | K | 01_AE | Total |
|---|---|---|---|---|---|---|---|---|---|---|---|
| A | 12,472 | 24 | 38 | 80 | 7 | 97 | 71 | 28 | 8 | 248 | 13,073 |
| B | 75 | 117,780 | 205 | 198 | 96 | 25 | 7 | 11 | 28 | 157 | 118,582 |
| C | 24 | 70 | 13,218 | 7 | 19 | 6 | 14 | 8 | 12 | 1 | 13,379 |
| D | 34 | 25 | 5 | 3,621 | 34 | 3 | 8 | 6 | 39 | 3 | 3,778 |
| F | 4 | 16 | 1 | 2 | 1,274 | 7 | 1 | 2 | 19 | 1 | 1,327 |
| G | 43 | 34 | 4 | 1 | 17 | 2,263 | 25 | 10 | 9 | 2 | 2,408 |
| H | 16 | 0 | 1 | 1 | 13 | 18 | 152 | 15 | 1 | 0 | 217 |
| J | 3 | 0 | 1 | 6 | 17 | 6 | 11 | 69 | 11 | 1 | 125 |
| K | 0 | 0 | 0 | 0 | 9 | 0 | 3 | 0 | 27 | 0 | 39 |
| 01_AE | 48 | 56 | 16 | 7 | 2 | NA | 1 | NA | 1 | 8,381 | 8,512 |
| Total | 12,719 | 118,005 | 13,489 | 3,923 | 1,488 | 2,425 | 293 | 149 | 155 | 8,794 | 161,440 |

(f) Confusion table (LANL on the left, the present invention at the top) after outlierness filtering (O < 2.0)

| | A | B | C | D | F | G | H | J | K | 01_AE | Total |
|---|---|---|---|---|---|---|---|---|---|---|---|
| A | 12,162 | 20 | 38 | 67 | 1 | 48 | 0 | 0 | 0 | 118 | 12,454 |
| B | 68 | 116,278 | 204 | 147 | 53 | 6 | 1 | 0 | 0 | 121 | 116,878 |
| C | 22 | 63 | 13,071 | 3 | 12 | 1 | 1 | 0 | 0 | 1 | 13,174 |
| D | 30 | 22 | 4 | 3,492 | 5 | 2 | 1 | 0 | 0 | 2 | 3,558 |
| F | 3 | 16 | 1 | 2 | 914 | 5 | 1 | 0 | 1 | 0 | 943 |
| G | 35 | 33 | 4 | 0 | 9 | 1,744 | 0 | 0 | 0 | 0 | 1,825 |
| H | 14 | 0 | 1 | 1 | 4 | 6 | 24 | 0 | 0 | 0 | 50 |
| J | 3 | 0 | 1 | 2 | 6 | 2 | 1 | 0 | 0 | 0 | 15 |
| K | 0 | 0 | 0 | 0 | 5 | 0 | 0 | 0 | 6 | 0 | 11 |
| 01_AE | 44 | 52 | 15 | 5 | 0 | 0 | 0 | 0 | 0 | 8,094 | 8,210 |
| Total | 12,381 | 116,484 | 13,339 | 3,719 | 1,009 | 1,814 | 29 | 0 | 7 | 8,336 | 157,118 |

TABLE 2

Summary statistics of the benchmark test for HIV-1 M group and CRF01_AE protein sequences

| | A | B | C | D | F | G | H | J | K | 01_AE | Total |
|---|---|---|---|---|---|---|---|---|---|---|---|

(a) Number of gene segments per subtype before filtering

| Gene | A | B | C | D | F | G | H | J | K | 01_AE | Total |
|---|---|---|---|---|---|---|---|---|---|---|---|
| gag | 2,297 | 7,616 | 2,271 | 630 | 125 | 402 | 34 | 11 | 12 | 530 | 13,928 |
| pol | 2,740 | 47,937 | 4,377 | 1,028 | 747 | 1,021 | 74 | 56 | 8 | 4,301 | 62,289 |
| vif | 48 | 825 | 88 | 26 | 3 | 3 | — | 1 | — | 114 | 1,108 |
| vpr | 40 | 1,428 | 47 | 11 | 4 | 3 | — | 1 | — | 112 | 1,646 |
| tat | 64 | 1,558 | 209 | 40 | 3 | 2 | — | 1 | — | 112 | 1,989 |
| vpu | 45 | 909 | 155 | 12 | 4 | 12 | — | 1 | — | 142 | 1,280 |
| env | 6,044 | 43,500 | 4,748 | 1,720 | 400 | 867 | 92 | 44 | 21 | 2,684 | 60,120 |
| nef | 162 | 3,981 | 406 | 66 | 14 | 22 | 2 | 1 | 1 | 178 | 4,833 |
| Total | 11,440 | 107,754 | 12,301 | 3,533 | 1,300 | 2,332 | 202 | 116 | 42 | 8,173 | 147,193 |
| Dist. Acc. | 11,434 | 107,622 | 12,266 | 3,531 | 1,300 | 2,331 | 202 | 116 | 42 | 8,144 | 146,988 |

TABLE 2-continued

Summary statistics of the benchmark test for HIV-1 M group and CRF01_AE protein sequences

| | A | B | C | D | F | G | H | J | K | 01_AE | Total |
|---|---|---|---|---|---|---|---|---|---|---|---|
| (b) Number of gene segments per subtype after outlierness filtering (O < 2.0) |||||||||||||
| gag | 2,184 | 7,566 | 2,235 | 604 | 89 | 344 | 24 | 10 | 11 | 513 | 13,580 |
| pol | 2,370 | 44,394 | 4,162 | 942 | 425 | 776 | 31 | 17 | 3 | 3,991 | 57,111 |
| vif | 9 | 726 | — | — | — | 3 | — | — | — | — | 738 |
| vpr | 40 | 1,422 | 47 | 11 | 3 | 3 | — | 1 | — | 111 | 1,638 |
| tat | 63 | 1,552 | 209 | 40 | 3 | 1 | — | — | — | 111 | 1,979 |
| vpu | 45 | 906 | 154 | 12 | 2 | 12 | — | — | — | 140 | 1,271 |
| env | 5,766 | 43,416 | 4,690 | 1,571 | 306 | 641 | 50 | 19 | 11 | 2,597 | 59,067 |
| nef | 155 | 3,970 | 396 | 64 | 12 | 21 | 2 | 1 | 1 | 170 | 4,792 |
| Total | 10,632 | 103,952 | 11,893 | 3,244 | 840 | 1,801 | 107 | 48 | 26 | 7,633 | 140,176 |
| Dist. Acc. | 10,628 | 103,825 | 11,858 | 3,242 | 840 | 1,800 | 107 | 48 | 26 | 7,605 | 139,979 |
| (c) Subtype prediction concordance (%) with LANL Gold Standard before filtering |||||||||||||
| gag | 83.54 | 93.83 | 97.4 | 86.35 | 73.6 | 75.12 | 26.47 | 0 | 16.67 | 93.21 | 91.33 |
| pol | 65.44 | 96.49 | 95.98 | 86.38 | 85.54 | 59.94 | 60.81 | 23.21 | 12.5 | 93.14 | 93.84 |
| vif | 39.58 | 96.24 | 100 | 96.15 | 100 | 100 | — | 100 | — | 100 | 94.49 |
| vpr | 95 | 94.54 | 80.85 | 45.45 | 0 | 100 | — | 0 | — | 93.75 | 93.5 |
| tat | 96.88 | 100 | 100 | 87.5 | 100 | 100 | — | 100 | — | 99.11 | 99.6 |
| vpu | 93.33 | 98.68 | 95.48 | 91.67 | 50 | 100 | — | 100 | — | 95.77 | 97.58 |
| env | 95.09 | 99.47 | 98.04 | 92.56 | 75 | 84.2 | 34.78 | 20.45 | 52.38 | 99.66 | 98.17 |
| nef | 90.74 | 99.1 | 97.04 | 83.33 | 57.14 | 77.27 | 50 | 0 | 100 | 97.75 | 98.12 |
| Total | 85.38 | 97.64 | 97.11 | 89.3 | 80.54 | 72.08 | 43.07 | 21.55 | 35.71 | 95.62 | 95.62 |
| (d) Subtype prediction concordance (%) with LANL Gold Standard after outlierness filtering (O < 2.0) |||||||||||||
| gag | 87.32 | 94.14 | 98.12 | 86.26 | 66.29 | 72.67 | 0 | 0 | 9.09 | 93.18 | 92.28 |
| pol | 69.66 | 97.49 | 97.43 | 89.17 | 88.24 | 56.44 | 32.26 | 0 | 0 | 93.89 | 95.25 |
| vif | 0 | 100 | — | — | — | 100 | — | — | — | — | 98.78 |
| vpr | 95 | 94.87 | 80.85 | 45.45 | 0 | 100 | — | 0 | — | 94.59 | 93.89 |
| tat | 98.41 | 100 | 100 | 87.5 | 100 | 100 | — | — | — | 100 | 99.7 |
| vpu | 93.33 | 98.79 | 96.1 | 91.67 | 50 | 100 | — | — | — | 95.71 | 97.8 |
| env | 96.39 | 99.52 | 98.7 | 95.1 | 72.55 | 84.24 | 10 | 0 | 45.45 | 99.73 | 98.62 |
| nef | 93.55 | 99.27 | 99.49 | 82.81 | 50 | 80.95 | 50 | 0 | 100 | 98.24 | 98.6 |
| Total | 88.44 | 98.2 | 98.09 | 91.21 | 79.29 | 70.18 | 14.95 | 0 | 26.92 | 96.06 | 96.59 |
| (e) Confusion table (LANL on the left, the present invention at the top) before filtering |||||||||||||
| LANL |||||||||||||
| A | 9,767 | 95 | 248 | 105 | 98 | 250 | 104 | 26 | 34 | 713 | 11,440 |
| B | 100 | 105,213 | 603 | 1,056 | 264 | 44 | 77 | 54 | 152 | 191 | 107,754 |
| C | 88 | 83 | 11,945 | 26 | 41 | 40 | 14 | 17 | 9 | 38 | 12,301 |
| D | 36 | 182 | 51 | 3,155 | 17 | 10 | 10 | 45 | 12 | 15 | 3,533 |
| F | 19 | 76 | 51 | 8 | 1,047 | 37 | 5 | 2 | 48 | 7 | 1,300 |
| G | 289 | 54 | 100 | 15 | 74 | 1,681 | 23 | 10 | 16 | 70 | 2,332 |
| H | 57 | 12 | 9 | 6 | 13 | 15 | 87 | 1 | 1 | 1 | 202 |
| J | 14 | 8 | 22 | 5 | 10 | 16 | 12 | 25 | 4 | — | 116 |
| K | 1 | 1 | 7 | — | 10 | 7 | — | — | 15 | 1 | 42 |
| 01_AE | 199 | 53 | 39 | 1 | 6 | 39 | 13 | 5 | 3 | 7,815 | 8,173 |
| Total | 10,570 | 105,777 | 13,075 | 4,377 | 1,580 | 2,139 | 345 | 185 | 294 | 8,851 | 147,193 |
| (f) Confusion table (LANL on the left, the present invention at the top) after outlierness filtering (O < 2.0) |||||||||||||
| A | 9,403 | 90 | 228 | 96 | 67 | 142 | 5 | — | 4 | 597 | 10,632 |
| B | 78 | 102,076 | 580 | 883 | 149 | 25 | 11 | — | 4 | 146 | 103,952 |
| C | 79 | 79 | 11,666 | 21 | 14 | 18 | 1 | — | — | 15 | 11,893 |
| D | 30 | 173 | 49 | 2,959 | 9 | 8 | 2 | — | 1 | 13 | 3,244 |
| F | 17 | 72 | 48 | 6 | 666 | 24 | 2 | — | — | 5 | 840 |
| G | 271 | 54 | 95 | 14 | 40 | 1,264 | — | — | — | 63 | 1,801 |
| H | 51 | 12 | 9 | 5 | 3 | 10 | 16 | — | — | 1 | 107 |
| J | 13 | 7 | 12 | 5 | 5 | 6 | — | — | — | — | 48 |
| K | — | 1 | 7 | — | 6 | 4 | — | — | 7 | 1 | 26 |
| 01_AE | 183 | 51 | 38 | 1 | 6 | 20 | 1 | — | 1 | 7,332 | 7,633 |
| Total | 10,125 | 102,615 | 12,732 | 3,990 | 965 | 1,521 | 38 | — | 17 | 8,173 | 140,176 |

HCV sequences are now classified as genotypes 1 through 6 and their subtypes are suffixed by "a" through "k" (for example, 1a, 2k, 6h and so on). The multiple sequence alignments downloaded from the LANL website included only a few reference sequences per subtype, making it difficult to apply the present invention at the subtype level. As these genotypes were roughly equidistant from each other, the present invention was applied at the genotype level, lumping all the subtypes from a genotype together into a group. The results of the benchmark test for HCV nucleotide and protein sequences are listed in Tables 3 and 4, respectively.

TABLE 3

Summary statistics of the benchmark test for HCV nucleotide sequences

| | 1 | 2 | 3 | 4 | 5 | 6 | Total |
|---|---|---|---|---|---|---|---|
| (a) Number of gene segments per subtype before filtering | | | | | | | |
| gene | | | | | | | |
| 5utr | 1,533 | 306 | 662 | 406 | 56 | 332 | 3,295 |
| arfp | 2,803 | 313 | 581 | 234 | 21 | 434 | 4,386 |
| core | 4,090 | 469 | 720 | 275 | 30 | 492 | 6,076 |
| e1 | 15,248 | 1,699 | 2,251 | 1,680 | 309 | 341 | 21,528 |
| e2 | 18,271 | 1,827 | 2,348 | 1,209 | 286 | 166 | 24,107 |
| ns2 | 1,909 | 11 | 16 | 20 | 1 | 46 | 2,003 |
| ns3 | 2,764 | 65 | 271 | 22 | 107 | 46 | 3,275 |
| ns4a | 565 | 16 | 200 | 20 | 108 | 41 | 950 |
| ns4b | 746 | 11 | 42 | 20 | 108 | 41 | 968 |
| ns5a | 5,488 | 50 | 259 | 20 | 1 | 53 | 5,871 |
| ns5b | 3,299 | 453 | 504 | 442 | 122 | 334 | 5,154 |
| okamoto | 1,992 | 392 | 330 | 379 | 119 | 174 | 3,386 |
| p7 | 2,142 | 9 | 16 | 20 | 1 | 44 | 2,232 |
| Total | 60,850 | 5,621 | 8,200 | 4,747 | 1,269 | 2,544 | 83,231 |
| Dist. Acc. | 35,309 | 3,239 | 5,275 | 2,698 | 611 | 1,202 | 48,334 |
| (b) Number of gene segments per subtype after outlierness filtering (O < 2.0) | | | | | | | |
| 5utr | 1,340 | 234 | 392 | 16 | 0 | 265 | 2,247 |
| arfp | 2,790 | 308 | 578 | 142 | 3 | 393 | 4,214 |
| core | 4,082 | 462 | 690 | 258 | 15 | 474 | 5,981 |
| e1 | 15,227 | 1,567 | 2,250 | 1,533 | 250 | 339 | 21,166 |
| e2 | 18,119 | 1,499 | 1,934 | 798 | 222 | 157 | 22,729 |
| ns2 | 1,877 | 11 | 16 | 0 | 1 | 38 | 1,943 |
| ns3 | 2,762 | 65 | 269 | 0 | 4 | 45 | 3,145 |
| ns4a | 565 | 16 | 157 | 1 | 37 | 20 | 796 |
| ns4b | 743 | 11 | 36 | 0 | 3 | 41 | 834 |
| ns5a | 5,471 | 50 | 220 | 0 | 1 | 53 | 5,795 |
| ns5b | 3,249 | 383 | 465 | 4 | 3 | 317 | 4,421 |
| okamoto | 1,992 | 391 | 330 | 379 | 117 | 172 | 3,381 |
| p7 | 2,142 | 9 | 10 | 0 | 1 | 34 | 2,196 |
| Total | 60,359 | 5,006 | 7,347 | 3,131 | 657 | 2,348 | 78,848 |
| Dist. Acc. | 35,046 | 3,003 | 4,674 | 2,171 | 437 | 1,166 | 46,497 |
| (c) Subtype prediction concordance (%) with LANL Gold Standard before filtering | | | | | | | |
| 5utr | 94.98 | 96.73 | 90.48 | 86.45 | 98.21 | 48.8 | 88.59 |
| arfp | 99.79 | 98.08 | 99.48 | 100 | 100 | 99.54 | 99.61 |
| core | 99.49 | 97.01 | 99.72 | 98.18 | 100 | 98.98 | 99.23 |
| e1 | 99.13 | 99.12 | 99.91 | 61.37 | 44.34 | 99.41 | 95.48 |
| e2 | 97.15 | 61.9 | 99.06 | 31.84 | 19.58 | 80.72 | 90.36 |
| ns2 | 100 | 100 | 100 | 100 | 100 | 100 | 100 |
| ns3 | 100 | 98.46 | 100 | 100 | 100 | 100 | 99.97 |
| ns4a | 100 | 100 | 99 | 90 | 100 | 100 | 99.58 |
| ns4b | 100 | 100 | 92.86 | 100 | 100 | 100 | 99.69 |
| ns5a | 99.98 | 100 | 100 | 100 | 100 | 100 | 99.98 |
| ns5b | 97.3 | 99.78 | 99.4 | 99.55 | 98.36 | 99.7 | 98.1 |
| okamoto | 95.63 | 100 | 99.09 | 99.74 | 98.32 | 100 | 97.25 |
| p7 | 100 | 100 | 100 | 100 | 100 | 100 | 100 |
| Total | 98.47 | 86.78 | 98.74 | 67.6 | 67.93 | 91.67 | 95.27 |
| (d) Subtype prediction concordance (%) after outlierness filtering (O < 2.0) | | | | | | | |
| 5utr | 98.06 | 97.01 | 96.68 | 0 | — | 47.17 | 91.01 |
| arfp | 99.82 | 98.05 | 99.65 | 100 | 100 | 100 | 99.69 |
| core | 99.58 | 97.62 | 99.86 | 100 | 98.06 | 99.37 | 99.38 |
| e1 | 99.18 | 99.04 | 99.91 | 57.8 | 31.2 | 99.41 | 95.45 |
| e2 | 97.39 | 67.11 | 98.91 | 0 | 3.15 | 82.17 | 91.08 |
| ns2 | 100 | 100 | 100 | — | 100 | 100 | 100 |
| ns3 | 100 | 98.46 | 100 | — | 100 | 100 | 99.97 |
| ns4a | 100 | 100 | 99.36 | 0 | 100 | 100 | 99.75 |
| ns4b | 100 | 100 | 91.67 | — | 100 | 100 | 99.64 |
| ns5a | 99.98 | 100 | 100 | — | 100 | 100 | 99.98 |
| ns5b | 97.45 | 99.74 | 99.57 | 75 | 66.67 | 99.68 | 97.99 |
| okamoto | 95.63 | 100 | 99.09 | 99.74 | 98.29 | 100 | 97.25 |
| p7 | 100 | 100 | 100 | — | 100 | 100 | 100 |
| Total | 98.65 | 89.33 | 99.35 | 53.08 | 40.64 | 92.59 | 95.65 |
| (e) Confusion table (LANL on the left, the present invention at the top) before filtering | | | | | | | |
| LANL | | | | | | | |
| 1 | 59,916 | 748 | 69 | 28 | 17 | 72 | 60,850 |
| 2 | 592 | 4,878 | 58 | 28 | 13 | 52 | 5,621 |

TABLE 3-continued

Summary statistics of the benchmark test for HCV nucleotide sequences

| | | | | | | | |
|---|---|---|---|---|---|---|---|
| 3 | 24 | 33 | 8,097 | 28 | 7 | 11 | 8,200 |
| 4 | 1,260 | 63 | 183 | 3,209 | 14 | 18 | 4,747 |
| 5 | 24 | 11 | 180 | 1 | 862 | 191 | 1,269 |
| 6 | 169 | 6 | 32 | 1 | 4 | 2,332 | 2,544 |
| Total | 61,985 | 5,739 | 8,619 | 3,295 | 917 | 2,676 | 83,231 |

(f) Confusion table (LANL on the left, the present invention at the top) (outlierness < 2.0)

| | | | | | | | |
|---|---|---|---|---|---|---|---|
| 1 | 59,543 | 721 | 54 | 9 | — | 32 | 60,359 |
| 2 | 500 | 4,472 | 10 | 2 | 1 | 21 | 5,006 |
| 3 | 15 | 28 | 7,299 | — | — | 5 | 7,347 |
| 4 | 1,238 | 50 | 172 | 1,662 | — | 9 | 3,131 |
| 5 | 18 | 11 | 177 | — | 267 | 184 | 657 |
| 6 | 143 | 3 | 28 | — | — | 2,174 | 2,348 |
| Total | 61,457 | 5,285 | 7,740 | 1,673 | 268 | 2,425 | 78,848 |

| | Subtype | | | | | | |
|---|---|---|---|---|---|---|---|
| LANL | The present invention | Total tested | with LANL Agree | with LANL Disagree | No call | with the present invention Agree | with the present invention Disagree |

(g) Re-analyses of the mismatches in (f) with NCBI Genotyping Tool

| | | | | | | | |
|---|---|---|---|---|---|---|---|
| 2 | 1 | 141 | 106 | 31 | 4 | 30 | 107 |
| 4 | 1 | 1,165 | 3 | 1,142 | 20 | 1,137 | 8 |
| 6 | 1 | 137 | 63 | 7 | 67 | 7 | 63 |
| 1 | 2 | 268 | 23 | 222 | 23 | 222 | 23 |
| 4 | 3 | 88 | 0 | 88 | 0 | 87 | 1 |
| Total | | 1,799 | 195 | 1,490 | 114 | 1,483 | 202 |
| Concordance rate | | | 11.57% | | | 88.01% | |

(h) Re-analyses of the mismatches in (f) with REGA Genotyping Tool

| | | | | | | | |
|---|---|---|---|---|---|---|---|
| 2 | 1 | 141 | 102 | 30 | 9 | 24 | 108 |
| 4 | 1 | 1,165 | 19 | 1,128 | 18 | 1,128 | 19 |
| 6 | 1 | 137 | 87 | 2 | 48 | 0 | 89 |
| 1 | 2 | 268 | 7 | 250 | 11 | 231 | 26 |
| 4 | 3 | 88 | 4 | 84 | 4 | 84 | 0 |
| Total | | 1,799 | 219 | 1,494 | 90 | 1,467 | 242 |
| Concordance rate | | | 12.78% | | | 85.84% | |

TABLE 4

Summary statistics of the benchmark test for HCV protein sequences

| | 1 | 2 | 3 | 4 | 5 | 6 | Total |
|---|---|---|---|---|---|---|---|

(a) Number of gene segments per subtype before filtering

| gene | | | | | | | |
|---|---|---|---|---|---|---|---|
| arfp | 426 | 27 | 114 | 5 | 2 | 19 | 593 |
| core | 3,025 | 326 | 541 | 240 | 27 | 413 | 4,572 |
| e1 | 13,183 | 1,342 | 1,618 | 1,344 | 286 | 330 | 18,103 |
| e2 | 15,091 | 1,016 | 1,580 | 1,116 | 260 | 134 | 19,197 |
| ns2 | 2,100 | 411 | 286 | 468 | 37 | 131 | 3,433 |
| ns3 | 2,700 | 64 | 270 | 22 | 94 | 46 | 3,196 |
| ns4a | 535 | 16 | 199 | 20 | 95 | 41 | 906 |
| ns4b | 720 | 21 | 43 | 22 | 95 | 41 | 942 |
| ns5a | 5,036 | 51 | 261 | 20 | 1 | 53 | 5,422 |
| ns5b | 2,701 | 452 | 489 | 398 | 122 | 318 | 4,480 |
| okamoto | 2,563 | 404 | 397 | 360 | 121 | 230 | 4,075 |
| p7 | 1,398 | 602 | 17 | 42 | 1 | 45 | 2,105 |
| Total | 49,478 | 4,732 | 5,815 | 4,057 | 1,141 | 1,801 | 67,024 |
| Dist. Acc. | 28,052 | 2,565 | 3,521 | 1,924 | 520 | 1,054 | 37,636 |

(b) Number of gene segments per subtype after outlierness filtering (O < 2.0)

| | | | | | | | |
|---|---|---|---|---|---|---|---|
| arfp | 153 | 2 | 4 | 1 | NA | 5 | 165 |
| core | 2,892 | 315 | 510 | 227 | 20 | 391 | 4,355 |
| e1 | 13,030 | 1,297 | 1,605 | 1,248 | 28 | 326 | 17,534 |

TABLE 4-continued

Summary statistics of the benchmark test for HCV protein sequences

|  | 1 | 2 | 3 | 4 | 5 | 6 | Total |
|---|---|---|---|---|---|---|---|
| e2 | 13,840 | 860 | 889 | 624 | 90 | 107 | 16,410 |
| ns2 | 923 | 10 | 12 | NA | 1 | 38 | 984 |
| ns3 | 2,675 | 64 | 236 | NA | 22 | 35 | 3,032 |
| ns4a | 532 | 14 | 194 | NA | 41 | 30 | 811 |
| ns4b | 691 | 11 | 31 | NA | 22 | 40 | 795 |
| ns5a | 4,994 | 46 | 249 | NA | 1 | 53 | 5,343 |
| ns5b | 2,650 | 366 | 375 | 5 | 6 | 258 | 3,660 |
| okamoto | 2,452 | 401 | 397 | 354 | 119 | 230 | 3,953 |
| p7 | 1,133 | 8 | 13 | NA | 1 | 32 | 1,187 |
| Total | 45,965 | 3,394 | 4,515 | 2,459 | 351 | 1,545 | 58,229 |
| Dist. Acc. | 27,922 | 2,397 | 3,354 | 1,802 | 301 | 970 | 36,746 |
| (c) Subtype prediction concordance (%) with LANL Gold Standard before filtering | | | | | | | |
| arfp | 96.71 | 11.11 | 7.02 | 100.00 | 100.00 | 26.32 | 73.36 |
| core | 95.90 | 97.55 | 92.61 | 81.67 | 100.00 | 98.55 | 95.14 |
| e1 | 98.23 | 96.94 | 99.38 | 51.86 | 39.86 | 99.70 | 93.90 |
| e2 | 96.65 | 70.28 | 95.32 | 38.62 | 7.31 | 98.51 | 90.58 |
| ns2 | 74.29 | 34.06 | 6.99 | 4.70 | 5.41 | 35.11 | 52.14 |
| ns3 | 99.44 | 98.44 | 100.00 | 100.00 | 90.43 | 100.00 | 99.22 |
| ns4a | 99.81 | 100.00 | 98.99 | 100.00 | 92.63 | 97.56 | 98.79 |
| ns4b | 94.44 | 80.95 | 90.70 | 90.91 | 100.00 | 100.00 | 94.69 |
| ns5a | 99.98 | 98.04 | 100.00 | 100.00 | 100.00 | 100.00 | 99.96 |
| ns5b | 97.96 | 99.56 | 99.39 | 99.25 | 98.36 | 98.74 | 98.46 |
| okamoto | 94.97 | 99.75 | 99.24 | 99.44 | 98.35 | 100.00 | 96.64 |
| p7 | 81.40 | 60.13 | 94.12 | 47.62 | 100.00 | 95.56 | 75.06 |
| Total | 96.13 | 81.09 | 91.25 | 54.38 | 58.98 | 93.61 | 91.41 |
| (d) Subtype prediction concordance (%) after outlierness filtering (O < 2.0) | | | | | | | |
| arfp | 100.00 | 100.00 | 100.00 | 100.00 | NA | 100.00 | 100.00 |
| core | 99.65 | 97.78 | 95.88 | 82.38 | 100.00 | 99.23 | 98.14 |
| e1 | 99.28 | 98.84 | 99.88 | 48.24 | 100.00 | 99.69 | 95.68 |
| e2 | 97.51 | 75.35 | 93.25 | 0.00 | 1.11 | 100.00 | 91.90 |
| ns2 | 100.00 | 100.00 | 100.00 | NA | 100.00 | 100.00 | 100.00 |
| ns3 | 100.00 | 98.44 | 100.00 | NA | 95.45 | 100.00 | 99.93 |
| ns4a | 100.00 | 100.00 | 99.48 | NA | 97.56 | 100.00 | 99.75 |
| ns4b | 96.96 | 100.00 | 90.32 | NA | 100.00 | 100.00 | 96.98 |
| ns5a | 99.98 | 100.00 | 100.00 | NA | 100.00 | 100.00 | 99.98 |
| ns5b | 98.11 | 100.00 | 99.47 | 80.00 | 83.33 | 99.61 | 98.50 |
| okamoto | 97.72 | 100.00 | 99.24 | 99.72 | 99.16 | 100.00 | 98.46 |
| p7 | 100.00 | 100.00 | 100.00 | NA | 100.00 | 100.00 | 100.00 |
| Total | 98.74 | 93.08 | 97.96 | 46.64 | 73.50 | 99.68 | 96.03 |
| (e) Confusion table (LANL on the left, the present invention at the top) before filtering | | | | | | | |
| LANL | | | | | | | |
| 1 | 47,561 | 1,129 | 509 | 16 | 147 | 116 | 49,478 |
| 2 | 680 | 3,837 | 163 | 16 | 22 | 14 | 4,732 |
| 3 | 237 | 176 | 5,306 | 77 | 13 | 6 | 5,815 |
| 4 | 1,618 | 17 | 206 | 2,206 | 8 | 2 | 4,057 |
| 5 | 102 | 143 | 29 | 179 | 673 | 15 | 1,141 |
| 6 | 9 | 62 | 34 | 6 | 4 | 1,686 | 1,801 |
| Total | 50,207 | 5,364 | 6,247 | 2,500 | 867 | 1,839 | 67,024 |
| (f) Confusion table (LANL on the left, the present invention at the top) (outlierness < 2.0) | | | | | | | |
| 1 | 45,388 | 528 | 19 | — | 24 | 6 | 45,965 |
| 2 | 232 | 3,159 | 2 | 1 | — | — | 3,394 |
| 3 | 20 | 51 | 4,423 | 18 | — | 3 | 4,515 |
| 4 | 1,165 | 14 | 130 | 1,147 | 2 | 1 | 2,459 |
| 5 | 26 | 46 | 17 | — | 258 | 4 | 351 |
| 6 | 2 | 1 | 2 | — | — | 1,540 | 1,545 |
| Total | 46,833 | 3,799 | 4,593 | 1,166 | 284 | 1,554 | 58,229 |

Determination of MDS Dimensionality and Assessment of Model Validity

The discriminant models are built solely from the reference sequences and thus their validity is largely irrelevant to the query sequence itself. On the other hand, what gene and which portion of the genome the query corresponds to are critical to the discriminatory power as the phylogenetic signal varies along the genome. For a given variability in nucleotide sequences, the corresponding protein sequences may show quite different variability due to negative or positive selection. The present inventor addresses this issue by using the LOOCV error rates, which are measured by counting the reference sequences that are misclassified from the class prediction based on the rest of the references.

First the present inventor looked for the optimum MDS dimensionality, k, by surveying the error rates for each whole gene segment and, then, surveyed the error rates in sliding windows of each gene segment with that k. It is expected that the classification power of our discriminant models will increase by representing the sequences in higher and higher k. The misclassification error rate was surveyed from LOOCV runs by varying k from 1 through 50.

Figure 3:
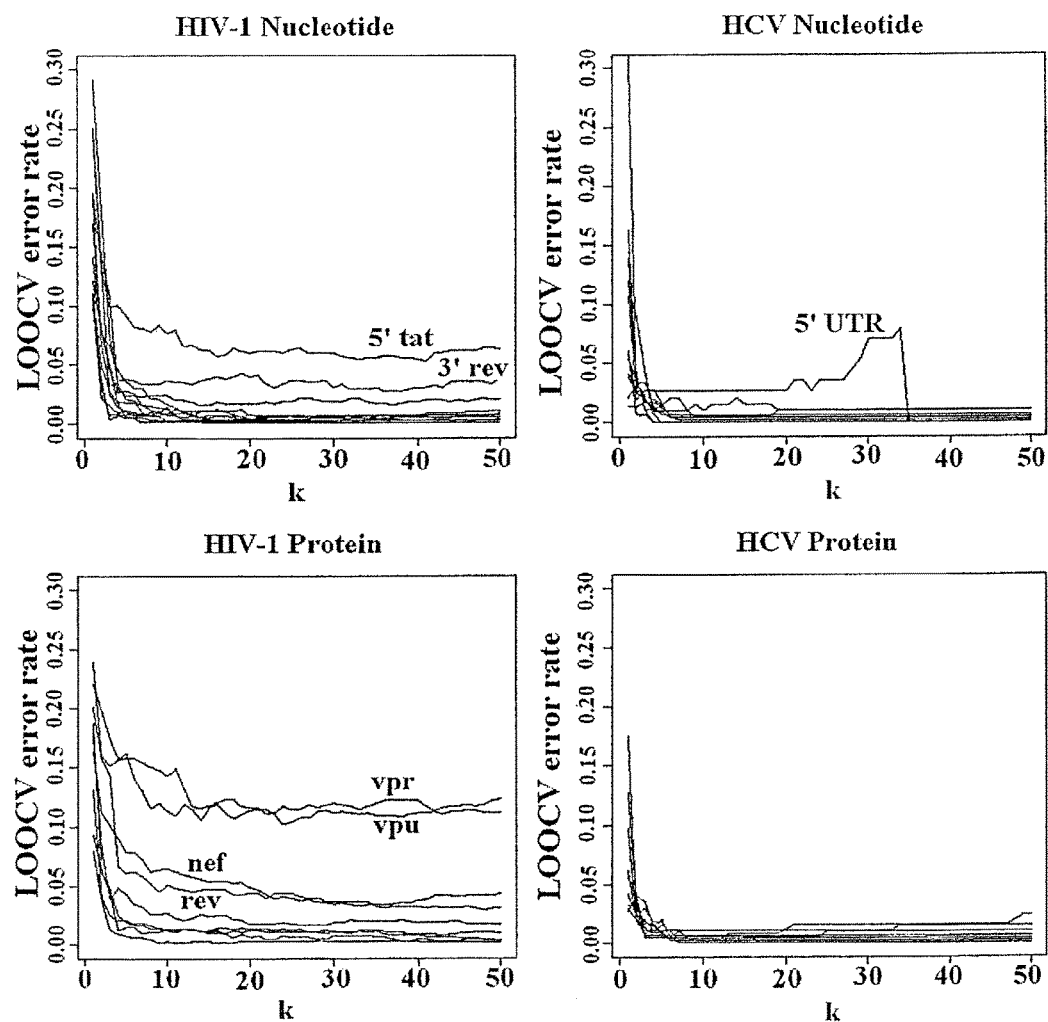
FIG. 3 shows surveys of LOOCV error rates by MDS dimensionality, k, for each gene segment. The LOOCV error rates of predicting genotypes (or subtypes) of references sequences were measured by varying the MDS dimensionally, k, from 1 through 50 for each gene segment of (a) HIV-1 nucleotide, (b) HIV-1 protein, (c) HCV nucleotide, and (d) HCV protein sequences. Some gene segments showing distinctively higher error rates are labeled. Regardless of sequence types, the error rates reached plateaus after k=10, which was used in the subsequent analyses.

As shown in FIG. 3, the error rates dropped quickly, reaching a plateau for k>=10. Except for HCV 5'-UTR nucleotide, HIV-1 5'-tat nucleotide and vpr/vpu protein sequences, excellent performance (error rate<5%) was observed with k>=10. HCV 5'-UTRs are known to be highly conserved, it would be difficult to classify them to genotypes. For HIV-1, short gene segments generally showed poorer performance. While there is no noticeable increase in computational overhead in incrementing k from 10 to 50, higher k might fall into overfitting. Therefore, k=10 was used throughout the analysis, although the prediction web server allowed changing this parameter.

Figure 4:
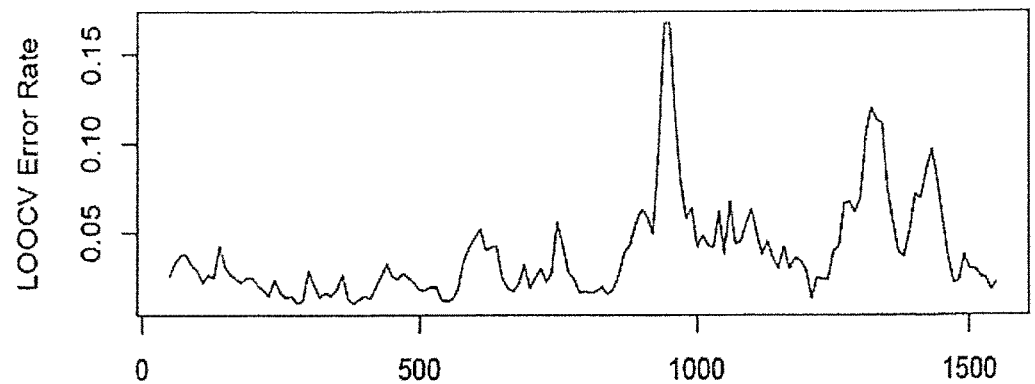
FIG. 4 shows Representative sliding window plots of LOOCV error rates along gene segments. The LOOCV error rates were plotted in sliding windows along the gene segments of (a) HIV-1 env nucleotide and (b) HCV e2 protein sequences. The MDS dimensionality was set at k=10 for both cases. The total list is shown in FIG. 8 and FIG. 9.
Figure 4:
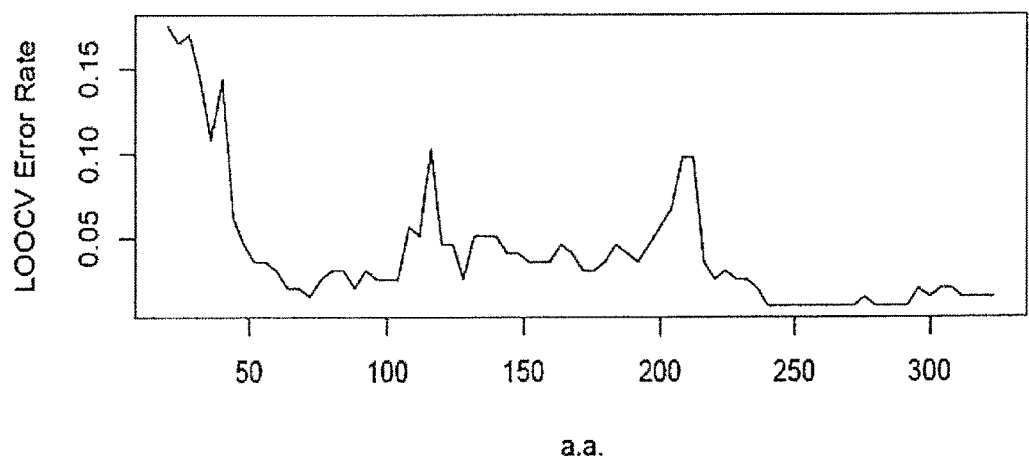

Then, the variation in discriminatory power along the genome or for each gene segment was measured by measuring LOOCV error rates in sliding windows (100 bp windows in 10 bp step or 40 aa windows in 4 aa step). Representative plots for HIV-1 env and HCV e2 are shown in FIG. 4 (see FIG. 8 and FIG. 9 for full listings). In general, the error rates were fairly low along the gene segment, although some distinct peaks were observed. The dominant peak seen in HIV-1 env corresponds to V3 loop and the profile of HCV e2 protein remarkably resembles the entropy plot that measured its sequence variability among 1b genotype. If the query sequence is composed of primarily of these regions, the high sequence variability is likely to cause suboptimal performance of the method of the present invention or any other genotyping tools. In tree-based methods, this will create branches composed of mixed genotypes (or subtypes). In such cases, the assessment of the clustering quality would be ambiguous.

On the other hand, the method of the present invention provides several means for quality assurance: a LOOCV error rate, posterior probabilities of membership, and an ability to inspect distribution of the sequences in multidimensional space. Even for the cases where the LOOCV error rate is around 10%, the genotyping (or subtyping) can be valid if the query is found in a region of the multidimensional space where the contaminations by the other genotypes (or subtypes) are minimal.

Performance Tests

The issue raised above would not be a serious problem as long as the major portion of the query contains good phylogenetic signals. This can be best addressed by running genotyping (or subtyping) runs, according to the present invention, for all the real world sequences and tabulating the LOOCV error rates. Table 5 shows the summary of such runs with all the non-recombinant nucleotide and protein sequences of HIV-1 and HCV. The LOOCV error rates were very low: mean and median being less than 5%. For HIV-1 nucleotide and HCV protein sequences, more than 90% of the cases had LOOCV error rates less than 3%, while the corresponding 90% percentiles of HCV nucleotide and HIV-1 protein were greater than 10%.

TABLE 5

Summary statistics of the benchmarking results[1]

| | Sequence type Virus | | | |
|---|---|---|---|---|
| | HIV-1[2] | | HCV | |
| | nucleotides | Proteins | nucleotides | Proteins |
| # of test sequences | 161,440 | 147,193 | 83,231 | 67,204 |
| LOOCV error rate | | | | |
| mean | 0.0133 | 0.0424 | 0.0237 | 0.0237 |
| median | 0.0068 | 0.0306 | 0.0050 | 0.0103 |
| 90% percentile | 0.0299 | 0.1088 | 0.1289 | 0.0268 |
| 99% percentile | 0.1415 | 0.1813 | 0.2566 | 0.2165 |
| MAP[3] (% of sequences higher than the cutoff) | | | | |
| P >= 0.99 | 95.8 | 84.8 | 91.5 | 93.7 |
| P >= 0.90 | 98.1 | 92.3 | 95.8 | 96.5 |
| P >= 0.50 | 99.9 | 99.5 | 99.9 | 99.8 |
| LANL concordance (% of sequences higher than the cutoff) | | | | |
| all | 98.7 | 95.6 | 95.3 | 91.4 |
| O <= 2.0 | 99.2 | 96.6 | 96.7 | 96.0 |

[1]Data as of Jan. 20, 2009.
[2]Major analysis (M-group and CRF01) only.
[3]Maximum a posteriori probability.

Having demonstrated that the linear models according to the present invention were well validated, then the posterior probability of classification was surveyed: more than 92% of the cases showed the maximum a posteriori probability values of 0.90 or higher, meaning unambiguous calls for most cases (Table 5). The overall concordance rates of the predictions according to the present invention with those retrieved from LANL for HIV-1 M-group and CRF01_AE sequences were higher than 95%, while those for HCV were better than 93% (Table 5).

The concordance rates for each gene and genotype (or subtype) are listed in Table 6 and 7 for HIV-1 and HCV nucleotide sequences, respectively (Details are shown in Table 1 and 3). If only a few reference sequences are available for any gene-subtype combination, the statistical model of subtype classification for that category would be unreliable: for example, only two to three references were available from each of subtypes H, J, and K. The test sequences in these categories were also extremely rare (Table 1(a) and 3(a)). Unless more sequences are discovered from these subtypes, their classification remains to be a challenge.

TABLE 6

The test results with HIV-1 nucleotide sequences[§]

| | All | | | Outlierness < 2.0 | | |
|---|---|---|---|---|---|---|
| Class | Total | Matched | % acc.* | Total | Matched | % acc.* |
| (a) by gene segment | | | | | | |
| gag | 15359 | 15006 | 97.70 | 15008 | 14,778 | 98.47 |
| pol | 65485 | 64483 | 98.47 | 62569 | 62,569 | 99.00 |
| vif | 1403 | 1382 | 98.50 | 1393 | 1,380 | 99.07 |
| vpr | 1715 | 1709 | 99.65 | 1704 | 1,698 | 99.65 |
| tat | 2586 | 2566 | 99.23 | 2569 | 2,553 | 99.38 |

TABLE 6-continued

The test results with HIV-1 nucleotide sequences[§]

| | All | | | Outlierness < 2.0 | | |
|---|---|---|---|---|---|---|
| Class | Total | Matched | % acc.* | Total | Matched | % acc.* |
| vpu | 1413 | 1398 | 98.94 | 1402 | 1,391 | 99.22 |
| env | 66185 | 65536 | 99.02 | 65287 | 64,889 | 99.39 |
| nef | 7294 | 7176 | 98.38 | 7186 | 7,151 | 99.51 |
| (b) by subtype | | | | | | |
| A | 13,073 | 12,472 | 95.40 | 12,454 | 12,163 | 97.66 |
| B | 118,582 | 117,776 | 99.32 | 116,878 | 116,282 | 99.49 |
| C | 13,379 | 13,218 | 98.80 | 13,174 | 13,071 | 99.22 |
| D | 3,778 | 3,621 | 95.84 | 3,558 | 3,492 | 98.15 |
| F | 1,327 | 1,274 | 96.01 | 943 | 914 | 96.92 |
| G | 2,408 | 2,263 | 93.98 | 1,825 | 1,744 | 95.56 |
| H | 217 | 152 | 70.05 | 50 | 24 | 48.00 |
| J | 125 | 69 | 55.20 | 15 | 0 | 0 |
| K | 39 | 27 | 69.23 | 11 | 6 | 54.55 |
| 01_AE | 8,512 | 8,381 | 98.46 | 8,210 | 8,094 | 98.59 |
| Total | 161,440 | 159,261 | 98.65 | 157,118 | 155,782 | 99.15 |

[§]Major analysis (M-group and CRF01) only.
*% accuracy given as 100 × Matched/Total, where Matched is the number cases concordant between the present invention and LANL.

TABLE 7

The test results with HCV nucleotide sequences

| | All | | | Outlierness < 2.0 | | |
|---|---|---|---|---|---|---|
| Class | Total | Matched | % acc.* | Total | Matched | % acc.* |
| (a) by gene segment | | | | | | |
| 5utr | 3,295 | 2,919 | 88.59 | 2,247 | 2,045 | 91.01 |
| arfp | 4,386 | 4,369 | 99.61 | 4,214 | 4,201 | 99.69 |
| core | 6,076 | 6,029 | 99.23 | 5,981 | 5,944 | 99.38 |
| e1 | 21,528 | 20,555 | 95.48 | 21,166 | 20,203 | 95.45 |
| e2 | 24,107 | 21,783 | 90.36 | 22,729 | 20,702 | 91.08 |
| ns2 | 2,003 | 2,003 | 100.00 | 1,943 | 1,943 | 100.00 |
| ns3 | 3,275 | 3,274 | 99.97 | 3,145 | 3,144 | 99.97 |
| ns4a | 950 | 946 | 99.58 | 796 | 794 | 99.75 |
| ns4b | 968 | 965 | 99.69 | 834 | 831 | 99.64 |
| ns5a | 5,871 | 5,870 | 99.98 | 5,795 | 5,794 | 99.98 |
| ns5b | 5,154 | 5,056 | 98.10 | 4,421 | 4,332 | 97.99 |
| okamoto | 3,386 | 3,293 | 97.25 | 3,381 | 3,288 | 97.25 |
| p7 | 2,232 | 2,232 | 100.00 | 2,196 | 2,196 | 100.00 |
| (b) by genotype | | | | | | |
| 1 | 60,850 | 59,919 | 98.47 | 60,359 | 59,544 | 98.65 |
| 2 | 5,621 | 4,878 | 86.78 | 5,006 | 4,472 | 89.33 |
| 3 | 8,200 | 8,097 | 98.74 | 7,347 | 7,299 | 99.35 |
| 4 | 4,747 | 3,209 | 67.60 | 3,131 | 1,662 | 53.08 |
| 5 | 1,269 | 862 | 67.93 | 657 | 267 | 40.64 |
| 6 | 2,544 | 2,332 | 91.67 | 2,348 | 2,174 | 92.59 |
| Total | 82,231 | 79,294 | 95.27 | 78,848 | 75,418 | 95.65 |

*% accuracy given as 100 × Matched/Total, where Matched is the number cases concordant between the present invention and LANL.

Outlier Filtering

Figure 5:
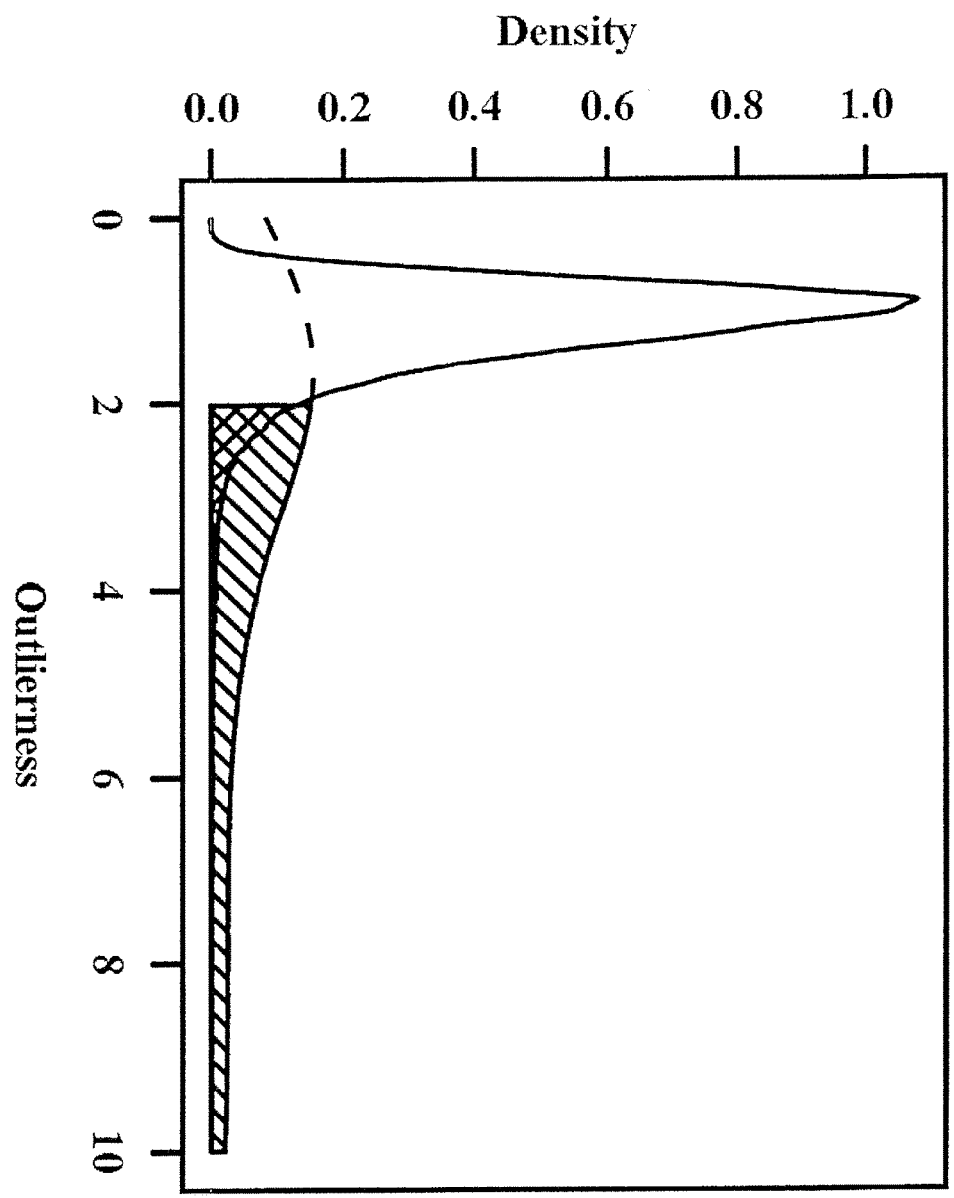
FIG. 5 shows the density distributions of the outlierness value, O, for the HIV-1 'major' analysis. Out of 161,440 cases tested, 159,261 predictions according to the method of the present invention were concordant with LANL subtype information (solid), while the rest were not (dashed).
Figure 10:
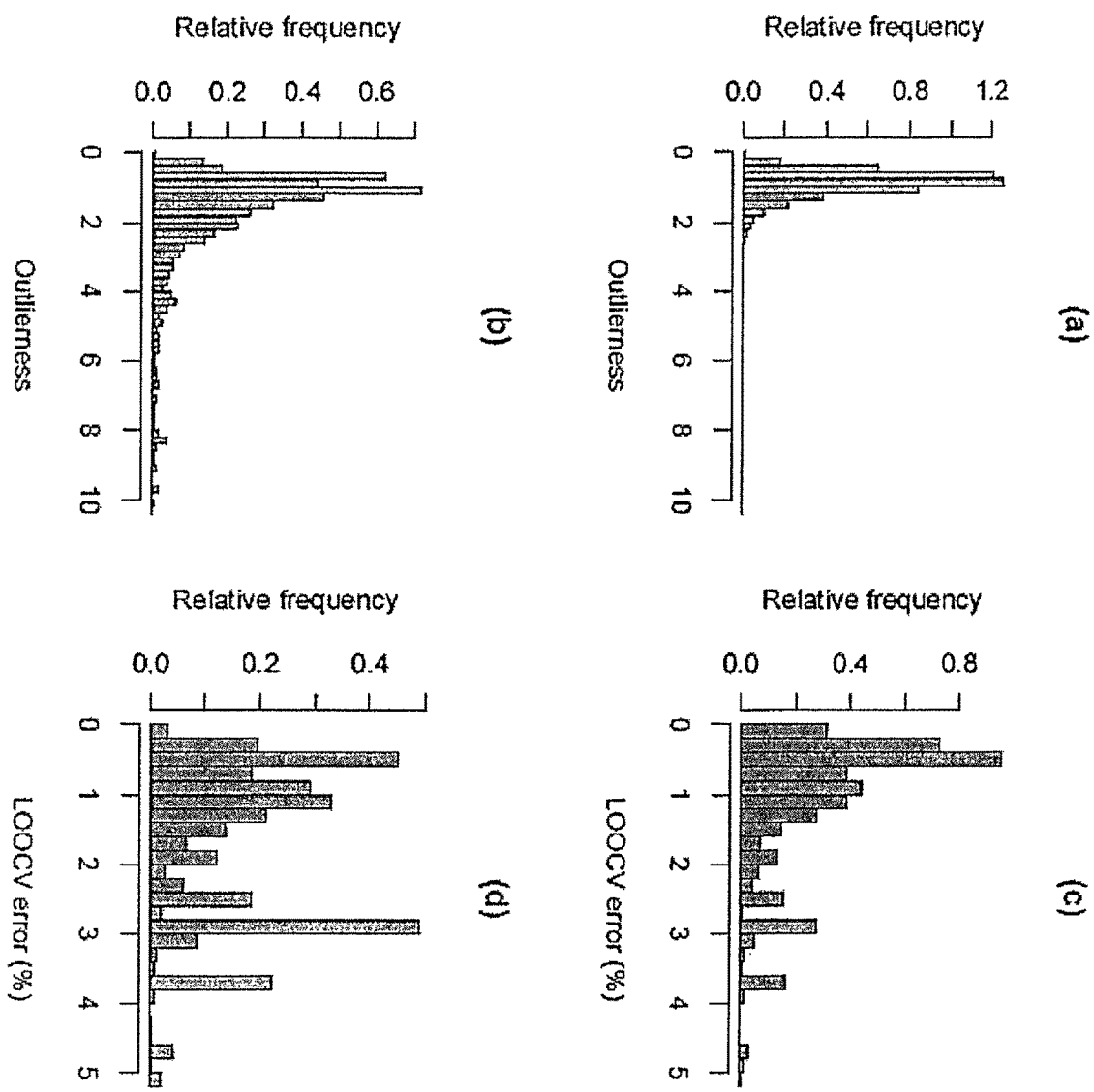
FIG. 10 shows the histograms of outlierness values and LOOCV error rates for the HIV-1 'major' analysis. The distribution of outlierness value for which the predictions based on the present invention agreed with LANL showed a sharp peak centered around 1.0 (a), while those disagreed showed a very long tail up to 10.0 (b). After filtering out low confidence cases (outlierness<2.0) there still remained relatively more cases having higher error rates for the discordant predictions (d) than the concordant ones (c). However, their proportion was not much and any filtering scheme based on these values has not been implemented.

Having proposed the outlierness value, O (Eq. 1), as an indicator of how well the query clustered with the corresponding references, its distribution was examined: the density plots of O showed a sharp peak centered around 1.0 for the concordant predictions (solid line), while a long tail up to 10.0 were observed for discordant cases (dashed line) (FIG. 5) (See also FIG. 10 for the related histograms). It appears that cutoff at O=2.0 would eliminate more than half the misclassifications with a minimal sacrifice of concordant predictions. Since the overall concordance rates were already very high, only marginal improvement was seen with nucleotide sequences. However, more noticeable improvement was seen with protein sequences (Table 5). The most significant improvements in the concordance rates were seen for HIV-1 gag and pot protein sequences (from 91.3% and 93.8% to 92.2% and 95.2%, respectively) and HCV e2 and ns2 protein sequences (from 90.6% and 52.1% to 91.9% and 100%, respectively).

Assessment of the HIV-1 Nested Analysis Results

Many HIV-1 sequences have been described as circulating recombinant forms (CRFs) by LANL. For a total of 9,145 nucleotide gene segments from a total of 8,719 such sequences, subtypes were assigned by the 'nested' analysis according to the present invention. After the 'major' analysis, the subtypes having posterior probability greater than 0.01 were collected and the CRFs originated from these subtypes were added to the pool. The CFR reference sequences derived from the subtypes were also added to the pool.

The classification procedure according to the present invention was, then, applied to the pool of references. A total of 5,068 nucleotide gene segment sequences passed the filtering step (O≤2.0) and had unambiguous calls (posterior probability 0.99), with an overall accuracy of 93.6% (Table 8; Statistical results for protein sequence is shown in Table 9). It should be noted that the number of reference sequences per gene segment or subtype is not high for CRFs presently and consequently the accuracy reported herein should be interpreted carefully.

TABLE 8

Benchmark results of HIV-1 recombinant nucleotide sequences from 'nested' analysis

| | All | | | Outlierness < 2.0 & P > 0.99 | | |
|---|---|---|---|---|---|---|
| Category | Total | Matched | % acc. | Total | Matched | % acc. |
| (a) by gene segment | | | | | | |
| gag | 1,459 | 961 | 65.87 | 817 | 758 | 92.78 |
| pol | 4,090 | 3,428 | 83.81 | 2,450 | 2,359 | 96.29 |
| vif | 30 | 19 | 63.33 | 20 | 14 | 70.00 |
| vpr | 23 | 12 | 52.17 | 7 | 7 | 100.00 |
| tat | 28 | 19 | 67.86 | 8 | 8 | 100.00 |
| vpu | 29 | 16 | 55.17 | 11 | 9 | 81.82 |
| env | 3,389 | 2,786 | 82.21 | 1,722 | 1,570 | 91.17 |
| nef | 97 | 35 | 36.08 | 33 | 16 | 48.48 |
| (b) by subtype | | | | | | |
| 02_AG | 5,197 | 4,637 | 89.22 | 4,048 | 4,000 | 98.81 |
| 03_AB | 267 | 42 | 15.73 | 96 | 0 | 0.00 |
| 04_cpx | 23 | 15 | 65.22 | 4 | 4 | 100.00 |
| 05_DF | 27 | 20 | 74.07 | 5 | 5 | 100.00 |
| 06_cpx | 1,111 | 791 | 71.20 | 116 | 111 | 95.69 |
| 07_BC | 664 | 467 | 70.33 | 221 | 163 | 73.76 |
| 08_BC | 279 | 116 | 41.58 | 65 | 23 | 35.38 |
| 09_cpx | 56 | 35 | 62.50 | 8 | 7 | 87.50 |
| 10_CD | 191 | 66 | 34.65 | 36 | 1 | 2.78 |
| 11_cpx | 709 | 590 | 83.22 | 275 | 273 | 99.27 |
| 12_BF | 332 | 313 | 94.28 | 145 | 140 | 96.55 |
| 13_cpx | 170 | 143 | 84.12 | 9 | 5 | 55.56 |
| 14_BG | 98 | 30 | 30.61 | 32 | 4 | 12.50 |
| 15_01B | 14 | 6 | 42.86 | 5 | 2 | 40.00 |
| 16_A2D | 7 | 5 | 71.43 | 3 | 3 | 100.00 |
| Total | 9,145 | 7,276 | 79.56 | 5,068 | 4,741 | 93.55 |

TABLE 9

Benchmark results of HIV-1 recombinant protein sequences from 'nested' analysis

| | All | | | Outlierness < 2.0 & P > 0.99 | | |
|---|---|---|---|---|---|---|
| Category | Total | Matched | % acc. | Total | Matched | % acc. |
| (a) by gene segment | | | | | | |
| gag | 1,357 | 754 | 55.56 | 247 | 219 | 88.66 |
| pol | 3,897 | 2,766 | 70.98 | 958 | 842 | 87.89 |
| vif | 30 | 16 | 53.33 | 3 | 0 | 0.00 |
| vpr | 25 | 8 | 32.00 | 1 | 1 | 100.00 |
| tat | 25 | 14 | 56.00 | 6 | 6 | 100.00 |
| vpu | 26 | 12 | 46.15 | 7 | 6 | 85.71 |
| env | 3,318 | 2,276 | 68.60 | 771 | 726 | 94.16 |
| nef | 56 | 30 | 53.57 | 12 | 9 | 75.00 |
| (b) by subtype | | | | | | |
| 02_AG | 5,096 | 3,912 | 76.77 | 1,327 | 1,234 | 92.99 |
| 03_AB | 270 | 50 | 18.52 | 6 | 0 | 0.00 |
| 04_cpx | 22 | 9 | 40.91 | 2 | 2 | 100.00 |
| 05_DF | 27 | 12 | 44.44 | 5 | 1 | 20.00 |
| 06_cpx | 1,031 | 451 | 43.74 | 52 | 38 | 73.08 |
| 07_BC | 572 | 401 | 70.10 | 133 | 115 | 86.47 |
| 08_BC | 218 | 65 | 29.81 | 14 | 2 | 14.29 |
| 09_cpx | 55 | 19 | 34.55 | 5 | 1 | 20.00 |
| 10_CD | 154 | 31 | 20.13 | 19 | 0 | 0.00 |
| 11_cpx | 692 | 483 | 69.80 | 300 | 295 | 98.33 |
| 12_BF | 325 | 298 | 91.69 | 81 | 75 | 92.59 |
| 13_cpx | 168 | 127 | 75.60 | 44 | 41 | 93.18 |
| 14_BG | 87 | 16 | 18.39 | 16 | 5 | 31.25 |
| 15_01B | 13 | 0 | 0 | 1 | 0 | 0.00 |
| Total | 8,734 | 5,876 | 62.28 | 2,005 | 1,809 | 90.22 |

The high accuracy seen with pol sequences (Tables 8 and 9) are encouraging as the genes in this segment are the targets of antiviral therapies and recent resistance screenings to help guide treatment regimens generate increasing number of these sequences.

Even with this success, there were still many sequences that failed to pass filtering steps. As a classification tool, the present invention has been developed to assign a subtype among a set of known subtypes, and thus not designed to detect a new subtype.

However, the present invention may hint some important clues for the analysis of these outlier sequences in terms of outlierness value and a set of posterior probabilities. For the definitive recombinant analysis, bootscanning or sliding-window analysis along the sequence is necessary.

Process for Subtype Decision

It is evident from the aforementioned that one has to accept the prediction results if and only if the reported parameters such as posterior probability (P) and outlierness (O) are reasonable. A working proposal for highly confident genotype (or subtype) assignment may be P better than 0.99 and O less than 2.0. A straightforward application of such criteria to HCV sequences achieved a false positive rate around 2.6%, leaving about 13.6% as undecided.

The subtype decision for a HIV-1 sequence is not as straightforward as the genotyping a HCV sequence as the former has to deal with the issue of recombinant forms. The present inventor showed that the present invention achieved high classification accuracies with HIV-1 sequence sets that had been pre-segregated as non-recombinants or CRFs. In real situations, prior to the analysis, whether the query is recombinant or not was not known. The present invention runs a 'major' analysis and subsequently a 'nested' one. An automated decision process is, then, needed in order to summarize those statistics in an orderly manner. For example, if the results from the 'major' and 'nested' analyses are different, the user may be confused. Here, the objective of the present invention is to maximize the accuracy without sacrificing the prediction coverage too much. Based on the filtering criteria mentioned above, the present inventor proposes the following strategy: (i) accept the result from 'nested' analysis only if its clustering is tight (O≤2.0) and the posterior probability is greater than or equal to 0.99; (ii) otherwise, accept the result only if the 'major' and 'nested' analyses agree with each other and one of the outlierness values is less than or equal to 2.0; or (iii) accept the result from 'major' analysis if its outlierness value is less than or equal to 1.0 and the P value is greater than or equal to 0.99. The present inventor applied this strategy to 177,198 HIV-1 nucleotide sequences (gene segments), for which the subtype information were available from LANL (Table 10). A total of 138,452 sequences passed the first step with 98.9% accuracy, while the second step applied to the 38,746 leftovers from step (i) yielded 27,401 sequences with 94.6% accuracy. This heuristic decision scheme resulted in 98.0% overall prediction accuracy for 94.2% of the total sequences, leaving out 10,248 sequences without subtype assignment (5.8%). Although one might try an alternative strategy that maximizes the prediction coverage at the loss of the accuracy, the approach according to the present invention is the one minimizes misclassification and leaves the 'twilight zone' to the users' discretion.

TABLE 10

Accuracy and coverage of each subtype decision step for HIV-1 nucleotide gene segments

| Sequence set* | Description | No. of sequences | Accuracy (%) | Coverage (%) |
|---|---|---|---|---|
| 1 | Subtypes given by LANL | 177,198 | | 100 |
| 2 | [Nested analysis] Outlierness < 2.0 & Pval > 0.99 among (1) | 138,452 | | 78.1 |
| | Correctly classified among (2) | 136,956 | 98.92 | |
| 3 | (1) − (2) | 38,746 | | 21.9 |
| 4 | Outlierness < 2.0 & Subtype(major) = subtype(nested) among (3) | 27,401 | | 15.5 |
| | Correctly classified among (4) | 25,927 | 94.62 | |
| 5 | (3) − (4) | 10,248 | | 6.4 |
| 6 | [Major analysis] Outlierness < 1.0 & Pval > 0.99 among (5) | 1,097 | | 0.6 |
| | Correctly classified among (6) | 797 | 72.65 | |
| 7 | (5) − (6) | 10,248 | | 5.8 |
| 8 | Subtype assigned (2) + (4) + (6) | 166,950 | | 94.2 |
| | Correctly classified among (8) | 163,680 | 98.04 | |

TABLE 10-continued

Accuracy and coverage of each subtype decision step for HIV-1 nucleotide gene segments

| Sequence set* | Description | No. of sequences | Accuracy (%) | Coverage (%) |
|---|---|---|---|---|
| 9 | (1) – (8) | 10,248 | | 5.8 |
| | Pval < 0.6 among (9) | 392 | | 0.2 |
| | Outlierness > 10.0 among (9) | 817 | | 0.5 |

*The sequence sets 2, 4, and 6 correspond to the decision steps (i), (ii), and (iii) in the main text, respectively.

Comparison with Other Methods

The present inventor has validated the performance of the present invention in genotyping HCV and subtyping HIV-1 sequences against the de facto gold standard available from LANL databases. As the present invention shows excellent performance with either nucleotide or protein sequences, it would be informative to compare with other automatic genotyping (or subtyping) methods.

Most conventional methods report concordance rates with LANL similar to those of the present invention, even though one of the tests showed quite discordant results among those methods. However, their test cases were quite limited, not as full scale as those of the present invention. It should also be emphasized that all those methods are based on well-established core algorithms in the fields of sequence alignment or phylogenetics. As such, appropriate implementations of those methods should work well for the classification of the query, as long as it is well clustered with only one of the genotypes (or subtypes).

Therefore, it would be more informative to understand the difference of these methods in dealing with a problematic query sequence that is either divergent or recombinant. As there are no such test panels publicly available, the present inventor has devised my own panels: one panel of sequences for which the present invention and LANL did not agree and the other sequences the present invention considered outliers.

The present inventor validated the result with independent runs with REGA, one of the most sophisticated subtyping tools (Table 11 for details). The agreement between the present invention and REGA was excellent when both made confident predictions (96.6% concordance rate). REGA employs a series of check points to reject problematic cases: for example, REGA does not assign a subtype if the bootstrap value is too low or the query is outside or basal to the subtype cluster.

TABLE 11

REGA results of the mismatches between the present invention and LANL for HIV-1 nucleotide sequences

| Category | All | | Outlierness < 2.0 | |
|---|---|---|---|---|
| Total cases compared | 1,214 | 100% | 414 | 100% |
| REGA agreed with the present invention | 309 | 73.22% | 227 | 96.60% |
| REGA disagreed with the present invention | 113 | 26.78% | 8 | 3.40% |
| Failed to pass confidence checks by REGA | 792 | 65.24% | 179 | 43.24% |

Out of 1,214 such cases for which REGA results were able to be retrieved, about ⅔ failed to pass those confidence checks by REGA. About the same number of cases also failed the outlierness test by the present invention (O>2.0). However, the consensus between these two filtering results was not high as there were 179 out of 414 cases that passed the present inventions, but not REGA's, filter. Although they constituted only 0.1% of all the HIV-1 benchmark test cases, thorough understanding may be important in light of the forthcoming rise of such cases. These presumably fall into the cases where subtyping methods relying on small number of references (two to four per subtype) cannot assign definitive subtypes to the query, but methods like the present invention can make predictions qualified with statistical significances.

The confusion table revealed several situations where the numbers of misclassification cases were resistant to the outlierness filtering: for example, more than 1,200 sequences originally assigned to genotype 4 by LANL were predicted as genotype 1 by the present invention (Table 3(e) and 3(f)). Independent tests of these cases with the NCBI genotyping tool and REGA have produced higher concordance rates with the present invention results (85~88%) than with the LANL results (11~13%) (Table 3(g) and (h)). Further analyses of these cases in more detail may be necessary. Nevertheless, the present invention was successfully tested with HCV.

Figure 6:
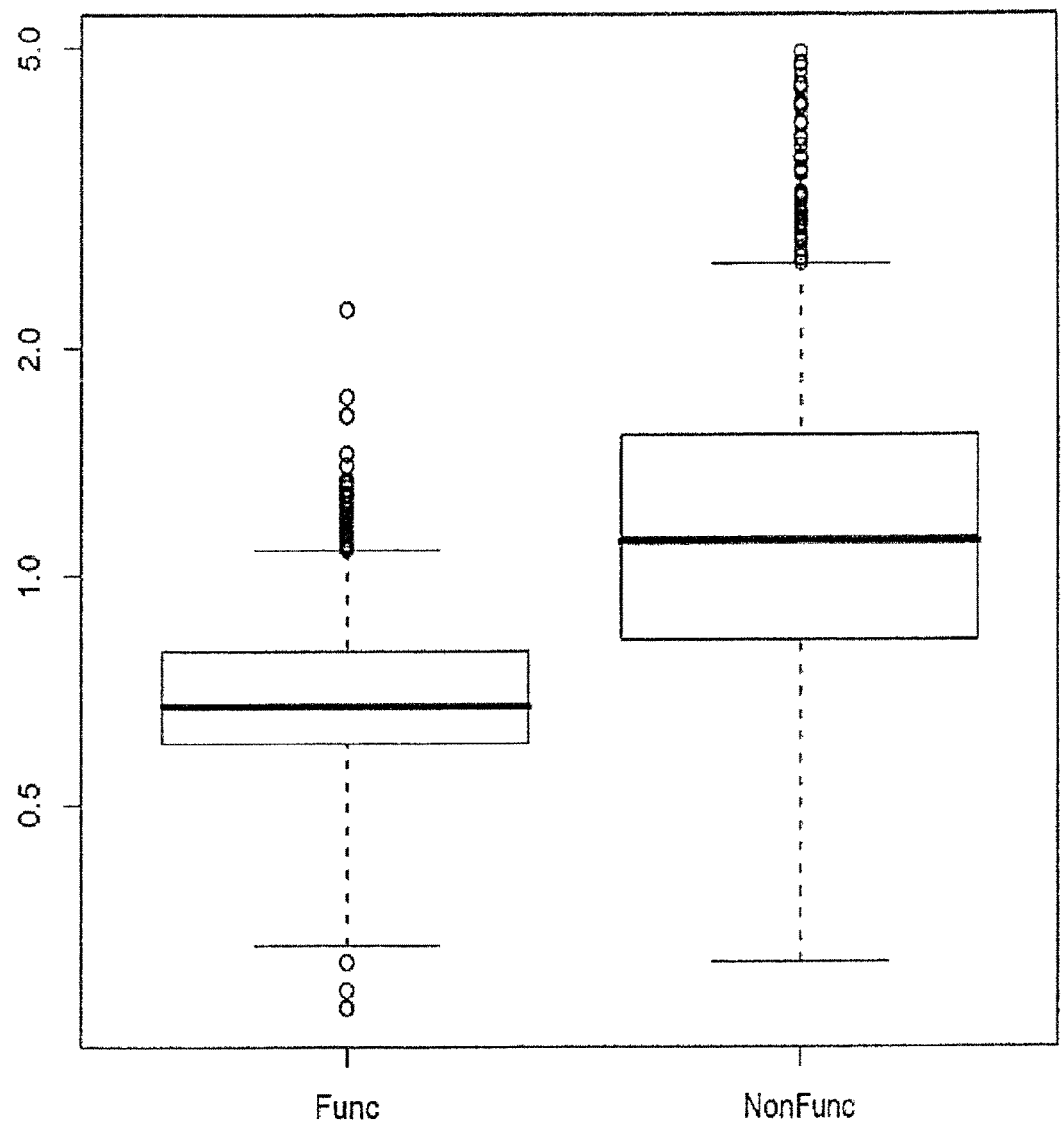
FIG. 6 shows a boxplot of the outlierness values for HIV-1 hypermutated sequences. The boxplot of the outlierness, O, parameters were drawn for 561 non-functional and 1,519 functional sequences reported by previous studies (Janini M, Rogers M, Birx D R, McCutchan F E: Human immunodeficiency virus type 1 DNA sequences genetically damaged by hypermutation are often abundant in patient peripheral bolld mononuclear cells and may be generated during near-simultaneous infection and activation of CD4(+) T cells. *J Virol* 2001, 75(17): 7973-7986; Gandhi S K, Siliciano J D, Bailey J R, Siliciano R F, Blankson J N: Role of APOBEC3G/F-mediated hypermutation in the control of human immunodeficiency virus type 1 in elite suppressors. *J Virol* 2008, 82(6): 3125-3130; Land A M, Ball T B, Luo M, Pilon Rm, Sandstrom P, Embree J E, Wachihi C, Kimani J, Plummer F A: Human immunodeficiency virus (HIV) type 1 proviral hypermutation correlates with CD4 count in HIV-infected women from Kenya. *J Virol* 2008, 82(16): 8172-8182) that specifically labeled whether each sequence was 'nonfunctional' or not.

Hypermutation creates quasi-species that are distant from their ancestors and are often with loss of function in the component genes. It would be interesting to see how the present invention behalves with such sequences. There were 14 reports of HIV-1 hypermutations whose sequences had been deposited with the public archives. Among 2,308 such sequences, 2,279 were identified from our benchmark results. Since the sequences with non-functional gene components are likely more divergent than the intact sequences, the present inventor would compare the degree of divergence between the two groups that have originated from the same studies. Among those 14 reports, three specifically labeled whether the sequence was non-functional or not. The outliernesses, O, parameter for 561 non-functional and 1,519 functional sequences were measured. As shown in FIG. 6, the former had distinctively higher O values than the latter. This demonstrates that the present invention may be useful in pre-screening hypermutation.

Hereinafter, an example analysis of a hypermutated sequence with other tools is described. Janini et al. described a 297 bp HIV-1 pol gene coding a non-functional protease due to hypermutation (GenBank accession AY036374.1 and GI: 15192372) (Janini M, Rogers M, Birx D R, McCutchan F E: Human immunodeficiency virus type 1 DNA sequences genetically damaged by hypermutation are often abundant in patient peripheral blood mononuclear cells and may be generated during near-simultaneous infection and activation of CD4(+) T cells. *J Virol*, 2001, 75:7973-7986). The original GenBank record classified it to subtype A. Although NCBI Genotyping Tool also classified it as distinct subtype A, there was no obvious indication of hypermutation. REGA HIV Subtyping Tool assigned it to subtype A with rather high bootstrap (74%), although the topological shape of the phylogenetic tree was unusual. The present invention also classified it to subtype A with high confidence (P=1.0) but more than 10-fold distant than the known subtype A references ($O_{group}$=10.56). Compared to the maximum radius encompassed by all 735 reference sequences, it was almost four-fold divergent ($O_{all}$=3.99).

The invention claimed is:

1. A computer system for classifying genotype or subtype of a query sequence, the system comprising:
   one or more databases that store information on classified types of sequences of various viruses;
   a client computer that receives user inputs of the query sequence; and
   a web server comprising a processor and a memory, and coupled to the databases and the client computer via an Internet computer network,
   wherein the web server
   receives the query sequence from the client computer,
   selects, from the classified types stored in the databases, base sequences of various viruses of which genotypes or subtypes are known as reference sequences
   obtains a distance matrix by calculating distances between sequences in a multiple alignment of said reference sequences,
   develops a discriminant equation which classifies the reference sequences by performing discriminant analysis for a cluster obtained by clustering said reference sequences through multidimensional scaling of the distance matrix,
   classifies retroviral or flaviviral query sequence against the same type of virus, according to said discriminant equation, and
   provides the classified query sequence to the client computer, and
   wherein the client computer receives the classified query sequence and displays the classified query sequence on a screen of the client computer.

2. The system of claim 1, wherein said selecting further comprises removing indels from said multiple alignment.

3. The system of claim 1, wherein said multidimensional scaling of said developing is a principal coordinate analysis.

4. The system of claim 1, wherein said discriminant analysis of said developing is selected from the group consisting of a linear discriminant analysis and a quadratic discriminant analysis.

* * * * *

SEQUENCE LISTING

```
<160> NUMBER OF SEQ ID NOS: 1

<210> SEQ ID NO 1
<211> LENGTH: 560
<212> TYPE: DNA
<213> ORGANISM: HIV-1 virus

<400> SEQUENCE: 1
cctcaaatca ctctttggca acgaccacta gtcacaataa aagtagggg gcaactaaag        60 gaagctctat tagatacagg agcagatgat acagtattag aagaaacaga gttgccagga       120
agatggaaac caagaatgat aggggaatt ggaggtttta tcaaagtaag acagtatgat        180
cagatagtca tagaaatttg cggacataaa gctgtaggta cagtattagt aggacctaca       240
cctgtcaaca taattggaag aaatttgttg actcagattg gctgcacttt aaattttccc      300
atcagtccta ttgaaactgt accagtaaaa ttaaagccag gaatggatgg cccaaaagtt      360
aaacagtggc cattgacaga agaaaaaata aaagcattag tagaaatttg tacagaaatg      420
gaaaaggaag gaaaaatttc aaaaattggg cctgaaaacc catacaatac tccagtattt      480
gccataaaga aaaaggacag tactaaatgg agaaaactag tggatttcag agagcttaat      540
aaaagaactc aagacttctg                                                  560
```